(12) United States Patent
Chen et al.

(10) Patent No.: US 10,377,757 B2
(45) Date of Patent: Aug. 13, 2019

(54) CRYSTAL FORM OF JAK INHIBITOR AND PREPARATION METHOD THEREOF

(71) Applicant: CRYSTAL PHARMATECH CO., LTD, Suzhou, Jiangsu (CN)

(72) Inventors: Minhua Chen, Jiangsu (CN); Yanfeng Zhang, Jiangsu (CN); Xiaojuan Diao, Jiangsu (CN); Nan Xia, Jiangsu (CN); Xiaoyu Zhang, Jiangsu (CN)

(73) Assignee: Crystal Pharmatech Co., Ltd., Suzhou (CN)

( * ) Notice: Subject to any disclaimer, the term of this patent is extended or adjusted under 35 U.S.C. 154(b) by 0 days.

(21) Appl. No.: 15/557,119

(22) PCT Filed: Mar. 11, 2016

(86) PCT No.: PCT/CN2016/076141
§ 371 (c)(1),
(2) Date: Sep. 10, 2017

(87) PCT Pub. No.: WO2016/141891
PCT Pub. Date: Sep. 15, 2016

(65) Prior Publication Data
US 2018/0044342 A1    Feb. 15, 2018

(30) Foreign Application Priority Data

Mar. 11, 2015  (CN) .......................... 2015 1 0106667
Apr. 21, 2015  (CN) .......................... 2015 1 0191070
(Continued)

(51) Int. Cl.
*C07D 487/04* (2006.01)
*A61K 31/519* (2006.01)
*A61P 29/00* (2006.01)

(52) U.S. Cl.
CPC .......... *C07D 487/04* (2013.01); *A61K 31/519* (2013.01); *A61P 29/00* (2018.01); *C07B 2200/13* (2013.01)

(58) Field of Classification Search
CPC ................................................... C07D 487/04
See application file for complete search history.

(56) References Cited

FOREIGN PATENT DOCUMENTS

| WO | 2009114512 A1 | 9/2009 |
| WO | 2015145286 A1 | 10/2015 |
| WO | 2015166434 A1 | 11/2015 |

OTHER PUBLICATIONS

B. Volk, et al., Crystalline forms of 1 ethylsulfonyl 3 4 7H pyrrolo 2 3 d pyrimidin 4 yl 1H pyrazol 1 yl azetidin 3 yl acetonitrile baricitinib, No. 27, 2015, IP.com IPCOM000244270D.

*Primary Examiner* — Marcos L Sznaidman
*Assistant Examiner* — Rayna Rodriguez
(74) *Attorney, Agent, or Firm* — VLP Law Group LLP; Kent H. Cheng

(57) ABSTRACT

The present disclosure relates to novel crystalline forms of JAK inhibitors and the preparation method thereof. The novel crystalline forms in the present disclosure can be used for the treatment of autoimmune diseases, particularly for the treatment of rheumatoid arthritis. The novel crystalline forms in the present disclosure have good stability and remarkable purification effect in process, moreover, its solubility and hygroscopicity meet the requirements for medical use. The preparation method of novel crystalline forms is simple, low cost, and has an important value for future optimization and development of the drug.

(Continued)

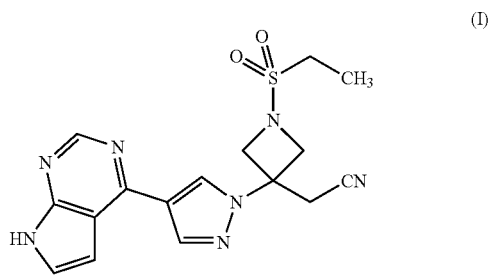 [SMILES: CCS(=O)(=O)N1CC(CC#N)(n2cc(-c3ncnc4[nH]ccc34)cn2)C1]
(I)
1 Claim, 12 Drawing Sheets
(30)  Foreign Application Priority Data
Jul. 17, 2015  (CN) .......................... 2015 1 0423070
Sep. 17, 2015  (CN) .......................... 2015 1 0591010

CRYSTAL FORM OF JAK INHIBITOR AND PREPARATION METHOD THEREOF

TECHNICAL FIELD

The present disclosure relates to the field of medicinal and pharmaceutical chemistry, particularly relates to crystalline forms of {1-(ethylsulfonyl))-3-[4-(7H-pyrrolo[2,3-d]pyrimidine-4-yl)-1H-pyrazol-1-yl]azetidine-3-yl} ac etonitrile and process of preparation thereof.

BACKGROUND

The JAK (Janus kinase) kinase is a non-receptor tyrosine kinase family in a cell, and the signal generated by the dielectric factor is transmitted through the JAK-STAT signal path. At present, there are four known JAK family members: JAK kinase 1 (JAK1), JAK kinase 2 (JAK2), JAK kinase 3 (JAK3) and Tyrosine kinase 2 (TYK2). The JAK-dependent cell factors participate in the pathogenic process of various inflammations and autoimmune diseases, JAK inhibitors can be widely used for treating various inflammatory diseases.

Baricitinib is a selective JAK1 and a JAK2 inhibitor developed by Lilly and Incyte. In kinase detection, the inhibition strength exhibited by Baricitinib aiming at JAK1 and JAK2 is 100 times higher than that of JAK3. Baricitinib is in clinical trial in the United States at present, and is used for treating rheumatoid arthritis. The chemical name of the medicine is {1-(ethylsulfonyl))-3-[4-(7H-pyrrolo[2,3-d]pyrimidine-4-yl)-1H-pyrazole-1-yl]azetidin-3-yl} ac etonitrile, and the structure is shown as Formula (I).

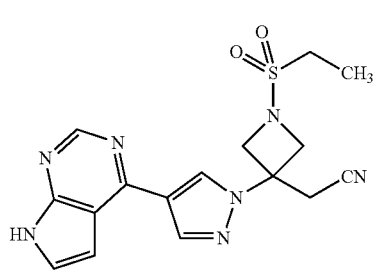

(I)

A certain pharmaceutical activity is of course the basic prerequisite to be fulfilled by a pharmaceutically active agent before same is approved as a medicament on the market. However, there are a variety of additional requirements a pharmaceutically active agent has to comply with. These requirements are based on various parameters which are connected with the nature of the active substance itself. Without being restrictive, examples of these parameters are the stability of the active agent under various environmental conditions, its stability during production of the pharmaceutical formulation and the stability of the active agent in the final medicament compositions.

The pharmaceutically active substance used for preparing the pharmaceutical compositions should be as pure as possible and its stability in long-term storage must be guaranteed under various environmental conditions. This is essential to prevent the use of pharmaceutical compositions which contain, in addition to the actual active substance, breakdown products thereof, for example. In such cases the content of active substance in the medicament might be less than that specified. In addition it is important that the pharmaceutically active substance be non-hygroscopic, stable both to degradation and subsequent changes to its solid form. This is important to facilitate the incorporation of the pharmaceutically active substance into pharmaceutical formulations. If the pharmaceutically active substance is hygroscopic ("sticky") in the sense that it absorbs water (either slowly or over time) it is almost impossible to reliably formulate the pharmaceutically active substance into a drug as the amount of substance to be added to provide the same dosage will vary greatly depending upon the degree of hydration. Furthermore, variations in hydration or solid form ("polymorphism") can lead to changes in physico-chemical properties, such as solubility or dissolution rate, which can in turn lead to inconsistent oral absorption in a patient. Preferably, therefore, a pharmaceutically active substance should be only slightly hygroscopic.

Accordingly, chemical stability, solid state stability, "shelf life" and materials handling properties (such as ease of solubilising the compound) of the pharmaceutically active substance are very important factors. In an ideal situation the pharmaceutically active substance and any compositions containing it, should be capable of being effectively stored over appreciable periods of time, without exhibiting a significant change in the physico-chemical characteristics of the active substance such as its activity, moisture content, solubility characteristics, solid form and the like. Further, the drug substance will usually require processing in order to achieve a particle size suitable for inhalation and any crystalline form must be stable during such processing so that the properties of the final product are predictable and reliable. In short, whether or not a compound is suitable for commercialisation as a drug is dependent on finding a form of the compound with a unique combination of properties determined according to the intended route of administration.

Since different crystalline forms of the same compound are significantly different in appearance, solubility, melting point, dissolution rate, bioavailability and the like, pharmaceutical stability, bioavailability and therapeutic effect will be affected. Therefore, the development of new crystalline forms more suitable for use in drug development has great significance.

As is known to those skilled in the art, the presence of new solid polymorphic forms of a known chemical substance is unpredictable. The existence of the polymorphic substance or the number of the polymorphic forms is also unpredictable. In addition, under what conditions to obtain a specific form, and how are the characteristics of the polymorphic form are also unpredictable. Since the properties of each polymorph of the polymorphic forms (e.g., solubility, stability) and thereby causing the difference of use and storage, it is necessary to study all solid forms, including all polymorphic forms to provide drugs with improved storage stability or predictable solubility.

Different crystalline forms cause different solubility and stability of the solid chemical drug, thus affecting the absorption and bioavailability of the drug, and can lead to difference in clinical efficacy. However, there is no report of the crystalline form of the compound of formula (I), and it is necessary to perform a comprehensive polymorph screening of the compound of formula (I) to select the most suitable form for development.

The inventor of the present disclosure has surprisingly found two crystalline forms of the compound of formula (I) and three phosphate crystalline forms in the research process. The crystalline forms in present disclosure have good stability, and the solubility and hygroscopicity meet the requirements for medical use, and the preparation method is simple, the cost is low, which is of great value for the future optimization and development of the drug.

SUMMARY

The present disclosure provides novel crystalline forms of the compound of formula (I) and novel crystalline forms of the salt and the process of preparation and application thereof.

One objective of the disclosure is to provide a crystalline form of a compound of formula (I), designated as Form I.

The crystalline Form I of the present disclosure, wherein the X-ray powder diffraction pattern shows characteristic peaks at 2theta values of 15.33°±0.20°, 16.66°±0.20° and 19.06°±0.20°. Furthermore, the crystalline Form I of the present disclosure, wherein the X-ray powder diffraction pattern further shows one or two or three characteristic peaks at 2theta values of 14.91°±0.20°, 16.25°±0.20° and 15.74°±0.20°. Preferably, the crystalline Form I of the present disclosure, wherein the X-ray powder diffraction pattern further shows characteristic peaks at 2theta values of 14.91°±0.20°, 16.25°±0.20° and 15.74°±0.20°.

Furthermore, the crystalline Form I of the present disclosure, wherein the X-ray powder diffraction pattern further shows one or two or three characteristic peaks at 2theta values of 25.51°±0.20°, 12.40°±0.20°, 17.39°±0.20°. Preferably, the crystalline Form I of the present disclosure, wherein the X-ray powder diffraction pattern further shows characteristic peaks at 2theta values of 25.51°±0.20°, 12.40°±0.20°, 17.39°±0.20°.

Preferably, the X-ray powder diffraction pattern of crystalline Form I of the present disclosure shows characteristic peaks at one or more position at 2theta values of 15.33±0.20°, 16.66±0.20°, 19.06±0.20°, 14.91°±0.20°, 16.25°±0.20°, 15.74°±0.20°, 25.51°±0.20°, 12.40°±0.20°, 17.39°±0.20°.

Furthermore, the crystalline Form I of the present disclosure, wherein the X-ray powder diffraction pattern of is substantially as depicted in FIG. 1.

The crystalline Form I of the present disclosure, wherein the differential scanning calorimetry thermogram (DSC) shows an endothermic peak when heated to about 212° C. (onset temperature), and the DSC thermogram is substantially as shown in FIG. 2.

The crystalline Form I of the present disclosure, wherein the thermal gravimetric analysis (TGA) thermogram displayed 0.8% weight loss when heated to 200° C., and the TGA thermogram is substantially as shown in FIG. 3.

Another objective of the present disclosure is to provide a process of preparing crystalline Form I, wherein the compound of formula (I) is added into one or more solvent systems selected from water, alcohols, ketones, esters, aromatic hydrocarbons, halogenated hydrocarbons, nitriles, nitroalkanes, cyclic ethers and aliphatic hydrocarbons, Form I was precipitated by anti-solvent addition, stirring, cooling crystallization or evaporation.

Furthermore, the alcohols solvent is preferably methanol, the ketones solvent is preferably acetone, the halogenated hydrocarbons is preferably dichloromethane.

Another objective of the disclosure is to provide a crystalline form of a compound of formula (I), designated as Form II.

The crystalline Form II of the present disclosure, wherein the X-ray powder diffraction pattern shows characteristic peaks at 2theta values of 18.00°±0.20°, 10.80°±0.20° and 7.26°±0.20°.

Furthermore, the crystalline Form II of the present disclosure, wherein the X-ray powder diffraction pattern future shows one or two or three characteristic peaks at 2theta values of 14.60°±0.20°, 12.14°±0.20° and 11.21°±0.20°. Preferably, the crystalline Form II of the present disclosure, wherein the X-ray powder diffraction pattern further shows characteristic peaks at 2theta values of 14.60°±0.20°, 12.14°±0.20° and 11.21°±0.20°.

Furthermore, the crystalline Form II of the present disclosure, wherein the X-ray powder diffraction pattern further shows one or two or three characteristic peaks at 2theta values of 22.59°±0.20°, 22.03°±0.20°, 19.64°±0.20°. Preferably, the crystalline Form II of the present disclosure, wherein the X-ray powder diffraction pattern further shows characteristic peaks at 2theta values of 22.59°±0.20°, 22.03°±0.20°, 19.64°±0.20°.

Preferably, the X-ray powder diffraction pattern of crystalline Form II of the present disclosure shows characteristic peaks at one or more position at 2theta values of 18.00°±0.20°, 10.80°±0.20°, 7.26°±0.20°, 14.60°±0.20°, 12.14°±0.20°, 11.21°±0.20°, 22.59°±0.20°, 22.03°±0.20°, 19.64°±0.20°.

Furthermore, the crystalline Form II of the present disclosure, wherein the X-ray powder diffraction pattern is substantially as depicted in FIG. 5.

The crystalline Form II of the present disclosure, wherein the differential scanning calorimetry thermogram (DSC) shows the first endothermic peak when heated to 144° C. (onset temperature), the second endothermic peak when heated to about 213° C., and the DSC thermogram is substantially as shown in FIG. 6.

The crystalline Form II of the present disclosure, wherein the thermal gravimetric analysis (TGA) thermogram displayed 16.5% weight loss when heated to 200° C., and the TGA thermogram is substantially as shown in FIG. 7.

Another objective of the present disclosure is to provide a process of preparing crystalline Form II, wherein the compound of formula (I) is added into glacial acetic acid or a mixture of glacial acetic acid and other solvents, Form II was precipitated by anti-solvent addition, evaporation, cooling crystallization or stirring.

Furthermore, other organic solvents comprise, but are not limited to water, alcohols, ketones, esters, aromatic hydrocarbons, halogenated hydrocarbons, nitriles, nitro alkanes, cyclic ethers or aliphatic hydrocarbons solvents.

Another objective of the present disclosure is to provide a pharmaceutical composition comprising an effective amount of of Form I or Form II or a combination thereof and pharmaceutically acceptable carrier, diluent or excipient. Generally, mix or contact therapeutically an effective amount of Form I or Form II or a combination thereof and more pharmaceutically acceptable excipients to make pharmaceutical composition or formulation, and the pharmaceutical composition or formulation are prepared by well-known method in the pharmaceutical field.

Use of the Form I or Form II or a combination thereof for preparing drugs treating autoimmune diseases, especially for preparing drugs treating rheumatoid arthritis.

The crystalline Form A of the present disclosure, wherein the X-ray powder diffraction pattern shows characteristic peaks at 2theta values of 17.22°±0.20°, 8.37°±0.20° and 3.59°±0.20°.

Furthermore, the crystalline Form A of the present disclosure, wherein the X-ray powder diffraction pattern future shows one or two or three characteristic peaks at 2theta values of 23.96°±0.20°, 19.40°±0.20° and 18.55°±0.20°. Preferably, the crystalline Form A of the present disclosure, wherein the X-ray powder diffraction pattern further shows characteristic peaks at 2theta values of 23.96°±0.20°, 19.40°±0.20° and 18.55°±0.20°.

Furthermore, the crystalline Form A of the present disclosure, wherein the X-ray powder diffraction pattern further shows one or two or three characteristic peaks at 2theta values of 7.78°±0.20°, 18.00°±0.20°, 25.40°±0.20°. Preferably, the crystalline Form A of the present disclosure, wherein the X-ray powder diffraction pattern further shows characteristic peaks at 2theta values of 7.78°±0.20°, 18.00°±0.20°, 25.40°±0.20°.

Preferably, the X-ray powder diffraction pattern of crystalline Form A shows characteristic peaks at one or more position at 2theta values of 17.22±0.20°, 8.37±0.20°, 3.59±0.20°, 23.96°±0.20°, 19.40°±0.20°, 18.55°±0.20°, 7.78°±0.20°, 18.00°±0.20°, 25.40°±0.20°.

Furthermore, the crystalline Form A of the present disclosure, wherein the X-ray powder diffraction pattern is substantially as depicted in FIG. 14

The crystalline Form A of the present disclosure wherein the differential scanning calorimetry thermogram (DSC) shows an endothermic peak when heated to about 187° C. (onset temperature), and the DSC thermogram is substantially as shown in FIG. 15.

The crystalline Form A of the present disclosure, wherein the thermal gravimetric analysis (TGA) thermogram displayed 1.3% weight loss when heated to 175° C., and the TGA thermogram is substantially as shown in FIG. 16.

Another objective of the present disclosure is to provide a process of preparing crystalline Form A wherein the compound of formula (I) and phosphate powder is added into a mixture solvent of multiple solvents, Form A was precipitated by stirring.

Furthermore, the mixed solvents comprise, but are not limited to alcohols, ketones, nitriles, cyclic ethers and aliphatic hydrocarbons solvent.

Furthermore, the mixed solvent is a mixture of acetonitrile and ethanol. The volume ratio of acetonitrile and ethanol is about 4:1 to 2:1. Preferably, the volume ratio of acetonitrile and ethanol is about 3:1.

Another objective of the present disclosure is to provide a novel phosphate crystalline form of the compound of formula (I), designated as Form B.

The crystalline Form B of the present disclosure, wherein the X-ray powder diffraction pattern shows characteristic peaks at 2theta values of 19.62°±0.20°, 16.73°±0.20° and 3.20°±0.20°.

Furthermore, the crystalline Form B of the present disclosure, wherein the X-ray powder diffraction pattern future shows one or two or three characteristic peaks at 2theta values of 16.21°±0.20°, 22.67°±0.20° and 25.85°±0.20°. Preferably, the crystalline Form B of the present disclosure, wherein the X-ray powder diffraction pattern further shows characteristic peaks at 2theta values of 16.21°±0.20°, 22.67°±0.20° and 25.85°±0.20°.

Furthermore, the crystalline Form B of the present disclosure, wherein the X-ray powder diffraction pattern further shows one or two or three characteristic peaks at 2theta values of 20.90°±0.20°, 17.53°±0.20° and 26.67°±0.20°. Preferably, the crystalline Form B of the present disclosure, wherein the X-ray powder diffraction pattern further shows characteristic peaks at 2theta values of 20.90°±0.20°, 17.53°±0.20°, 26.67°±0.20°.

Preferably, the X-ray powder diffraction pattern of crystalline Form B shows characteristic peaks at one or more position at 2theta values of 19.62°±0.20°, 16.73±0.20°, 3.20±0.20°, 16.21°±0.20°, 22.67°±0.20°, 25.85°±0.20°, 20.90°±0.20°, 17.53°±0.20°, 26.67°±0.20°.

Furthermore, the crystalline Form B of the present disclosure, wherein the X-ray powder diffraction pattern is substantially as depicted in FIG. 17.

The crystalline Form B of the present disclosure wherein the differential scanning calorimetry thermogram (DSC) shows an endothermic peak when heated to about 169° C. (onset temperature), and the DSC thermogram is substantially as shown in FIG. 18.

The crystalline Form B of the present disclosure, wherein the thermal gravimetric analysis (TGA) thermogram displayed 1.2% weight loss when heated to 160° C., and the TGA thermogram is substantially as shown in FIG. 19.

Another objective of the present disclosure is to provide a process of preparing crystalline Form B, wherein the compound of formula (I) and phosphate powder is added into a proper mixed crystallization solvent, Form B was precipitated by stirring. Furthermore, the appropriate crystallization solvents comprise, but are not limited to anhydrous alcohols, ketones, aromatic hydrocarbons, halogenated hydrocarbons, nitriles, nitro alkanes, and cyclic ethers solvents.

Furthermore, the ketones crystallization solvent is methyl isobutyl ketone, the esters crystallization solvent is isopropyl acetate.

Another objective of the present disclosure is to provide a novel phosphate crystalline form of a compound of formula (I), designated as Form C.

The crystalline Form C of the present disclosure, wherein the X-ray powder diffraction pattern shows characteristic peaks at 2theta values of 20.90°±0.20°, 18.01°±0.20° and 24.10°±0.20°.

Furthermore, the crystalline Form C of the present disclosure, wherein the X-ray powder diffraction pattern future shows one or two or three characteristic peaks at 2theta values of 15.30°±0.20°, 21.46°±0.20° and 14.62°±0.20°. Preferably, the crystalline Form C of the present disclosure, wherein the X-ray powder diffraction pattern further shows characteristic peaks at 2theta values of 15.30°±0.20°, 21.46°±0.20° and 14.62°±0.20°.

Furthermore, the crystalline Form C of the present disclosure, wherein the X-ray powder diffraction pattern further shows one or two or three characteristic peaks at 2theta values of 4.46°±0.20°, 22.83°±0.20° and 18.94°±0.20°. Preferably, the crystalline Form C of the present disclosure, wherein the X-ray powder diffraction pattern further shows characteristic peaks at 2theta values of 4.46°±0.20°, 22.83°±0.20°, 18.94°±0.20°.

Preferably, the X-ray powder diffraction pattern of crystalline Form C shows characteristic peaks at one or more position at 2theta values of 20.90±0.20°, 18.01±0.20°, 24.10±0.20°, 15.30°±0.20°, 21.46°±0.20°, 14.62°±0.20°, 4.46°±0.20°, 22.83°±0.20°, 18.94°±0.20°.

Furthermore, the crystalline Form C of the present disclosure, wherein the X-ray powder diffraction pattern is substantially as depicted in FIG. 20.

The crystalline Form C of the present disclosure wherein the differential scanning calorimetry thermogram (DSC) shows a small endothermic peak when heated to around 157° C., and show a sharp endothermic peak near the temperature of 178° C. (peak temperature), which is substantially as depicted in FIG. 21.

The crystalline Form C of the present disclosure, wherein the thermal gravimetric analysis (TGA) thermogram displayed 2.4% weight loss when heated to 162° C., and the TGA thermogram is substantially as shown in FIG. 22.

Another objective of the present disclosure is to provide a process of preparing crystalline Form C, wherein the compound of formula (I) and phosphate powder is added into a single solvent or a mixture of multiple solvents, Form C was precipitated by stirring.

Furthermore, the solvent comprises, but is not limited to a single solvent or a mixture of multiple solvents comprise one or more solvents, such as nitriles, water, alcohols, ketones, esters, aromatic hydrocarbons, halogenated hydrocarbons, nitro alkanes and cyclic ethers. Furthermore, the solvent is preferably water or a mixture of water and nitriles solvent. Furthermore, the mixture of water and nitriles solvent is a mixture of water and acetonitrile solvent.

Furthermore, the phosphate powder comprises the phosphate crystalline Form B.

The process of preparing crystalline Form B of the compound of formula (I) comprises that the compound of Formula (I) and phosphate powder is added into alcohols, ketones, nitriles, cyclic ethers and aliphatic hydrocarbons solvents, Form B was precipitated by stirring.

The X-ray powder diffraction pattern of the phosphate crystalline Form B of the compound of formula (I) shows characteristic peaks at one or more position at 2theta values of 19.62±0.20°, 16.73±0.20°, 3.20±0.20°, 16.21°±0.20°, 22.67°±0.20°, 25.85°±0.20°, 20.90°±0.20°, 17.53°±0.20°, 26.67°±0.20°.

Another objective of the present disclosure is to provide a process of preparing crystalline Form C, wherein the compound of formula (I) and concentrated phosphoric acid (14.6 mol/L) are added into a aqueous solvent to, Form C was precipitated by stirring.

Furthermore, the aqueous solvent comprises mixed solvent of the water and nitriles, alcohols, ketones, esters, aromatic hydrocarbons, halogenated hydrocarbons, nitro alkanes or cyclic ethers.

Another object of the disclosure is to provide a pharmaceutical composition, and the compositions comprises an effective treatment amount of phosphate Form A or phosphate Form B or phosphate Form C or a mixture of two or three of the above crystalline phosphate forms with one or more pharmaceutical adjuvants, the pharmaceutical composition or the preparation is prepared in a manner well known in the pharmacy field.

Furthermore, use of the phosphate Form A, phosphate Form B and phosphate Form C of the compound of Formula (I) or a mixture of two or three of the above crystalline phosphate forms for preparing drugs treating autoimmune diseases, especially for preparing drugs treating rheumatoid arthritis.

The pharmaceutical composition can be developed into a certain dosage form, and is administrated by a suitable route, such as oral administration and parenteral administration (including subcutaneous, muscle, vein or skin), rectal, transdermal, nasal and vagina, and the like. The dosage form suitable for oral administration comprises tablets, capsules, granules, powder and pills, a powder, an ingot, a solution, a syrup or a suspension according to needs, and can be used for rapid release, delayed release or regulation release of active pharmaceutical ingredients. The dosage form suitable for parenteral administration comprises an aqueous or non-aqueous sterile injection solution, an emulsion or a suspension. The dosage form suitable for rectal administration comprises a suppository or an enema. The dosage form suitable for transdermal administration comprises an ointment, a cream and a patch. The dosage form suitable for nasal administration comprises an aerosol, a spray and a nose drop The dosage form suitable for vaginal administration comprises a suppository, a plugging agent and a gel, a paste or a spray. Preferably, the crystalline forms of the present disclosure is especially suitable for preparing a tablet, a suspension, a capsule, a disintegrating tablet, an immediate release and controlled release tablet, and further preferably is a tablet, a suspension and a capsule.

The pharmaceutically acceptable excipient in the pharmaceutical composition is in the condition of a solid oral dosage form, including but not limited to: A diluent, such as starch, pregelatinized starch, lactose, powdery cellulose, microcrystalline cellulose, calcium hydrophosphate, tricalcium phosphate, mannitol, sorbitol, sugar and the like. An adhesive, such as arabic gum, guar gum, gelatin, polyvinylpyrrolidone, hydroxypropyl cellulose, hydroxypropyl methyl cellulose, polyethylene glycol and the like. A disintegrating agent, such as starch, sodium hydroxyacetate, pregelatinized starch, cross-linked povidone, cross-linked sodium carboxymethyl cellulose and colloidal silica. A lubricant, such as stearic acid, magnesium stearate, zinc stearate, sodium benzoate, sodium acetate and the the like. A glidants, such as colloidal silica and the like. A compound forming agent, such as various levels of cyclodextrin and resin. The release rate control agent, such as hydroxypropyl cellulose, hydroxymethyl cellulose, hydroxypropyl methyl cellulose, ethyl cellulose, methyl cellulose, methyl methacrylate, wax and the like. Other pharmaceutically acceptable excipients, including but not limited to: a film-forming agent, a plasticizer, a coloring agent, a flavoring agent, a viscosity regulator, a preservative, an antioxidant and the the like. Preferably, coating the tablet with a coating layer, for example, providing shellac isolation coating, sugar coating or polymer coating, wherein the coating layer comprises a polymer such as hydroxypropyl methyl cellulose, polyvinyl alcohol, ethyl cellulose, methacrylic acid polymer, hydroxypropyl cellulose or starch, and can also comprise an anti-sticking agent such as silicon dioxide, talcum powder, an emulsion agent such as titanium dioxide, a colorant such as an iron oxide colorant. In the case of a liquid oral dosage form, the appropriate excipient comprises water, oils, alcohols and glycols, a preservative, a stabilizer, a coloring agent and the like. The water or the non-water sterile suspension can contain a suspending agent and a thickening agent. The excipient that is suitable for the water-based suspension comprises synthetic rubber or natural rubber such as arabic gum, xanthium gum, alginate, glucan, sodium carboxymethyl cellulose, methylcellulose, polyvinylpyrrolidone or gelatin.

In the case of parenteral administration, the excipient of the water or non-aqueous sterile injectable solution is generally sterile water, normal saline or a glucose aqueous solution, which can contain a buffering agent, an antioxidant, a bacteriostatic agent and a solute capable of enabling the pharmaceutical composition to be combined with blood. Each excipient must be acceptable, and can be compatible with other ingredients in the formula and is harmless to a patient.

The pharmaceutically acceptable carrier in the pharmaceutical composition comprises, but is not limited to: single, double- or polysaccharide, sugar alcohol or another polyhydroxy compound. The appropriate carrier comprises sugar, starch and the like, such as lactose, sucrose, sorbitol sugar, mannitol, starch such as potato starch, corn starch or branched starch, cellulose derivatives and the like. The pharmaceutical composition can be obtained by methods known to those skilled in the art in the prior art. When preparing the pharmaceutical composition, the crystalline forms of the pharmaceutical composition is mixed with one or more pharmaceutically acceptable excipients, and mixed with one or more other active pharmaceutical ingredients. For example, the tablet, the capsule and the granule can be prepared through processes of mixing, granulating, tabletting or filling capsules. The powder is prepared by mixing active pharmaceutical ingredients and excipients which are ground into a proper size. The solution and the syrup can be prepared by dissolving the active pharmaceutical ingredients in a properly flavored water or aqueous solution. The suspension can be prepared by dispersing the active pharmaceutical ingredients in pharmaceutically acceptable carriers.

The crystalline form and the phosphate crystalline form of the compound of the present disclosure can be used as inhibitors of one or more JAK, and the activity of the JAK can be modulated through the dosage of the crystalline forms. The crystalline forms and phosphate crystalline forms of the compound of formula (I) can modulate the JAK, comprising any member of the JAK family, and the JAK is JAK2, JAK3 or TYK2. Preferably, the JAK is JAK1 or JAK2.

The crystalline forms and the phosphate crystalline forms of the compound of formula (I) of the present disclosure can be used for treating a JAK-associated disease or disorder in an individual (e.g., patient) by administering to the individual in need of such treatment a therapeutically effective amount or dose of crystalline forms or the phosphate crystalline forms of the compound or a pharmaceutical composition thereof. A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity. Further examples of JAK-associated diseases include autoimmune diseases such as multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, autoimmune thyroid disorders, and the like.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, melanoma etc.), hematological cancers (e.g., lymphoma, leukemia such as acute lymphoblastic leukemia, acute myelogenous leukemia (AML) or multiple myeloma), and skin cancer such as cutaneous T-cell lymphoma (CTCL) and cutaneous B-cell lymphoma. Example cutaneous T-cell lymphomas include Sezary syndrome and mycosis fungoides. Further JAK-associated diseases include inflammation and inflammatory diseases. Example inflammatory diseases include inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases.

The term "effective treatment amount" or "therapeutically effective amount" as used herein means that amount of an active compound that elicits the biological or medicinal response in a tissue, system, animal or human that is being sought by a researcher, veterinarian, medical doctor, or other clinician.

As used herein, the term "treatment" refers to one or more of the following:

(1) Preventing disease, for example, preventing the disease, illness or disorder in an individual who may be suffering from a disease, illness or disorder but not suffering from or displaying a lesion or symptom of the disease, (2) Inhibiting the disease, for example, inhibiting the disease, illness or disorder in an individual who is suffering from or displaying a lesion or symptom of the disease, illness or disorder, and (3) Improving the disease, for example, improving the disease, illness or disorder in an individual who is suffering from or displaying a lesion or symptom of the disease, illness or disorder (that is to reverse the lesion and/or symptoms), for example, reducing the severity of the disease.

As used herein, the term "polymorphic substance" refers to different crystalline forms of the same compound and includes, but is not limited to other solid forms including hydrates and solvates of the same compound. The phenomenon that the same drug molecule forms a variety of crystalline forms is called drug polymorphism, drug polymorphism is a phenomenon commonly found in solid drugs.

The term "X-ray powder diffraction pattern" as used herein refers to a diffraction pattern observed by an experiment or a parameter derived therefrom. The X-ray powder diffraction pattern is characterized by the peak position and the peak intensity The present disclosure has the following advantages:

At present, no crystalline form of the compound of formula (I) is reported in patents and literatures, but the inventor of the present disclosure broke through the problem, and found several new crystalline forms suitable for development.

The crystalline forms of the present disclosure are good in stability and remarkable purification effect in process. The crystalline forms can avoid crystal transformation during the storage and the development process, thus avoid the change of the bioavailability and the drug efficiency.

The crystalline forms of the present disclosure have low hygroscopicity and meet the bioavailability and efficacy requirements, and don't need a special drying condition in the preparation process. The preparation process and the post-treatment process of the drug are simplified. It is not easily affected by humidity, and is not harsh in requirement on storage conditions, and is convenient for long-term storage, so that the cost of material storage and quality control is greatly reduced, and the crystalline forms have very high economic value.

DETAILED DESCRIPTION OF THE DISCLOSURE

The present disclosure will be further explained by the specific embodiments, but are not intended to limit the scope of the present disclosure. The skilled in the art can make improvements to the process of preparation and the used instruments within the scope of the claims, and those improvements should be considered as falling into the scope of the present disclosure. Therefore, the protective scope of the present disclosure patent should be defined by the claims.

In the following examples, the test method is generally implemented according to a conventional condition or a condition that manufacturer recommends.

The abbreviations used in the disclosure are explained as follows:

XRPD: X-ray Powder Diffraction
DSC: Differential Scanning calorimetry
TGA: Thermal Gravimetric Analysis
DVS: Dynamic Vapor Sorption
$^1$H NMR: 1H Nuclear Magnetic Resonance X-ray powder diffraction pattern in the present disclosure was acquired by a Panalytical Empyrean X-ray powder diffractometer. The parameters of the X-ray powder diffraction method of the present disclosure were as follows:

X-ray Reflection: Cu, Kα
Kα1 (Å): 1.540598; Kα2 (Å): 1.544426
Kα2/Kα1 intensity ratio: 0.50
Voltage: 45 (kV)
Current: 40 (mA)
Scan range: from 3.0 degree to 40.0 degree Differential scanning calorimetry (DSC) data in the present disclosure were acquired by a TA Q2000. The parameters of the differential scanning calorimetry (DSC) method of the present disclosure were as follow:

Heating rate: 10° C./min
Purge gas: nitrogen

Thermal gravimetric analysis (TGA) data in the present disclosure were acquired by a TA Q5000. The parameters of the thermal gravimetric analysis (TGA) method of the present disclosure were as follow:

Heating rate: 10° C./min
Purge gas: nitrogen

Example 1

Process of Preparing Crystalline Form I of the Compound of Formula (I):

39.5 mg of compound of Formula (I) was added into 1.5 mL of acetone to obtain a suspension, then the suspension was put into a 50° C. constant temperature incubator and stirred for 100 minutes, filtered while was hot to obtain a clear solution, then the solution was slowly cooled to 5° C. at a rate of 0.1° C. per minute, centrifuged to give a solid, then the solid was placed at a constant temperature of 25° C. overnight for drying, the obtained solid was detected as crystalline Form I.

Figure 1:
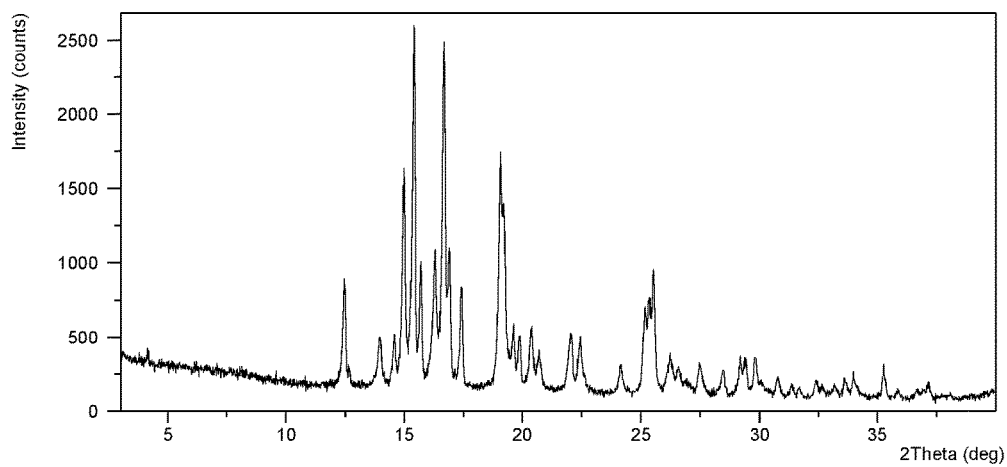
FIG. 1 shows an XRPD pattern of crystalline Form I
Figure 2:
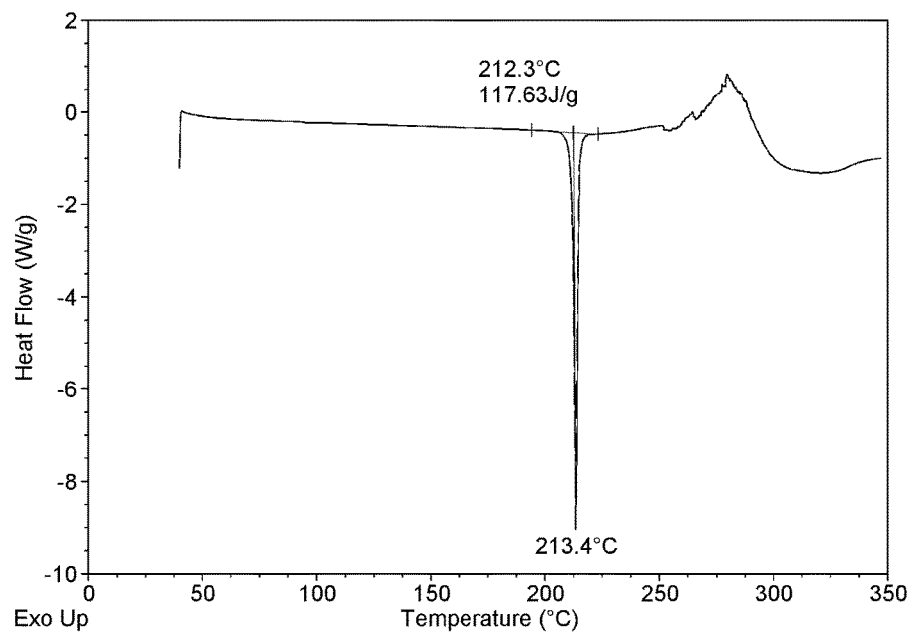
FIG. 2 shows a DSC thermogram of crystalline Form I
Figure 3:
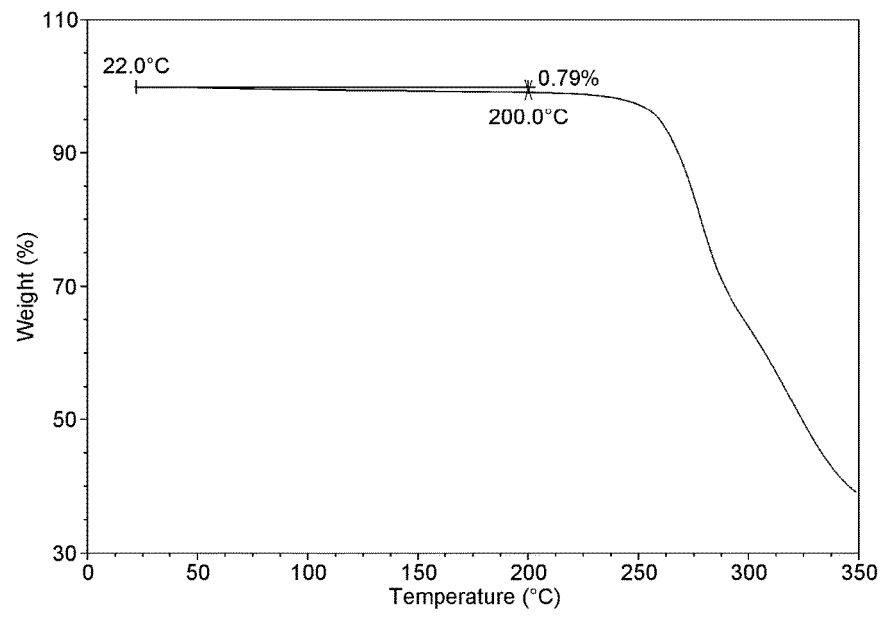
FIG. 3 shows a TGA thermogram of crystalline Form I

The XRPD datas of the solid prepared in this example are listed in Table 1. The XRPD pattern is displayed in FIG. 1. The DSC thermogram is displayed in FIG. 2, the TGA thermogram is displayed in FIG. 3

TABLE 1

| 2theta | d spacing | Relative intensity % |
|---|---|---|
| 4.14 | 21.35 | 3.97 |
| 12.46 | 7.10 | 28.61 |
| 13.96 | 6.35 | 13.61 |
| 14.58 | 6.08 | 14.56 |
| 14.97 | 5.92 | 59.98 |
| 15.39 | 5.76 | 100.00 |
| 15.68 | 5.65 | 34.24 |
| 16.27 | 5.45 | 38.33 |
| 16.66 | 5.32 | 94.55 |
| 16.88 | 5.25 | 38.62 |
| 17.39 | 5.10 | 28.27 |
| 19.06 | 4.66 | 64.93 |
| 19.20 | 4.62 | 51.06 |
| 19.60 | 4.53 | 16.15 |
| 19.87 | 4.47 | 14.94 |
| 20.37 | 4.36 | 16.94 |
| 20.69 | 4.29 | 10.35 |
| 22.03 | 4.03 | 15.63 |
| 22.43 | 3.96 | 15.50 |
| 24.14 | 3.69 | 7.46 |
| 25.16 | 3.54 | 23.41 |
| 25.51 | 3.49 | 33.04 |
| 26.23 | 3.40 | 10.01 |
| 26.56 | 3.36 | 6.90 |

TABLE 1-continued

| 2theta | d spacing | Relative intensity % |
|---|---|---|
| 27.47 | 3.25 | 8.05 |
| 28.45 | 3.14 | 6.62 |
| 29.18 | 3.06 | 9.44 |
| 29.39 | 3.04 | 9.93 |
| 29.81 | 3.00 | 10.45 |
| 30.76 | 2.91 | 5.05 |
| 31.36 | 2.85 | 3.06 |
| 31.69 | 2.82 | 2.04 |
| 32.40 | 2.76 | 4.13 |
| 33.20 | 2.70 | 2.80 |
| 33.62 | 2.67 | 4.66 |
| 33.99 | 2.64 | 5.61 |
| 35.24 | 2.55 | 8.54 |
| 35.85 | 2.50 | 1.86 |
| 37.12 | 2.42 | 3.93 |

Example 2

Process of Preparing Crystalline Form I of the Compound of Formula (I):

5.16 mg of the compound of Formula (I) was dissolved into 1.80 mL of dichloromethane, evaporating at room temperature, the obtained solid was detected as crystalline Form I. The XRPD datas of the solid prepared in this example are listed in Table 2.

TABLE 2

| 2theta | d spacing | Relative intensity % |
|---|---|---|
| 3.92 | 22.52 | 36.56 |
| 12.39 | 7.14 | 62.10 |
| 13.95 | 6.35 | 64.03 |
| 14.55 | 6.09 | 16.66 |
| 14.93 | 5.93 | 63.18 |
| 15.39 | 5.76 | 80.22 |
| 15.66 | 5.66 | 48.17 |
| 16.25 | 5.45 | 64.90 |
| 16.60 | 5.34 | 100.00 |
| 17.37 | 5.10 | 5.25 |
| 19.06 | 4.66 | 56.99 |
| 19.89 | 4.46 | 25.90 |
| 20.37 | 4.36 | 13.73 |
| 20.71 | 4.29 | 12.40 |
| 22.05 | 4.03 | 8.24 |
| 24.17 | 3.68 | 8.96 |
| 25.25 | 3.53 | 55.47 |
| 25.46 | 3.50 | 52.40 |
| 26.34 | 3.38 | 9.04 |
| 26.60 | 3.35 | 6.65 |
| 28.51 | 3.13 | 2.56 |
| 29.49 | 3.03 | 6.70 |
| 29.89 | 2.99 | 8.73 |
| 30.87 | 2.90 | 25.90 |
| 31.80 | 2.81 | 5.47 |
| 33.27 | 2.69 | 4.75 |
| 34.10 | 2.63 | 3.58 |
| 35.37 | 2.54 | 7.36 |
| 36.02 | 2.49 | 5.63 |
| 37.09 | 2.42 | 4.65 |

Example 3

Process of Preparing Crystalline Form II of the Compound of Formula (I):

106.3 mg of compound of Formula (I) was dissolved into 1.0 mL of glacial acetic acid, evaporating at room temperature, the obtained solid was detected as crystalline Form II.

Figure 5:
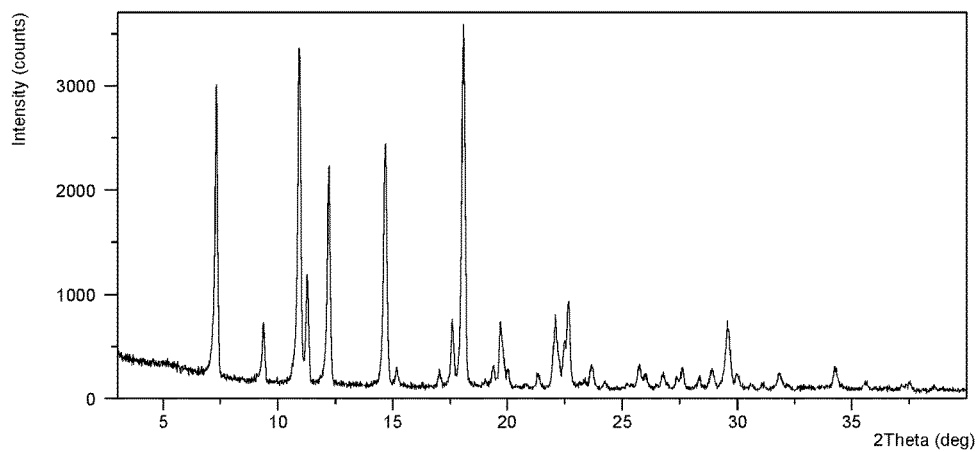
FIG. 5 shows an XRPD pattern of crystalline Form II
Figure 6:
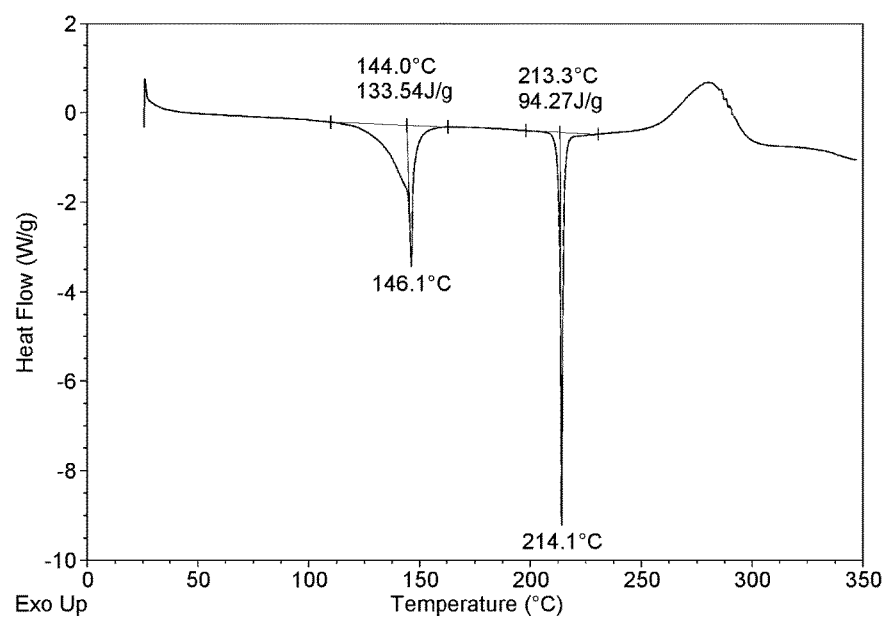
FIG. 6 shows a DSC thermogram of crystalline Form II
Figure 7:
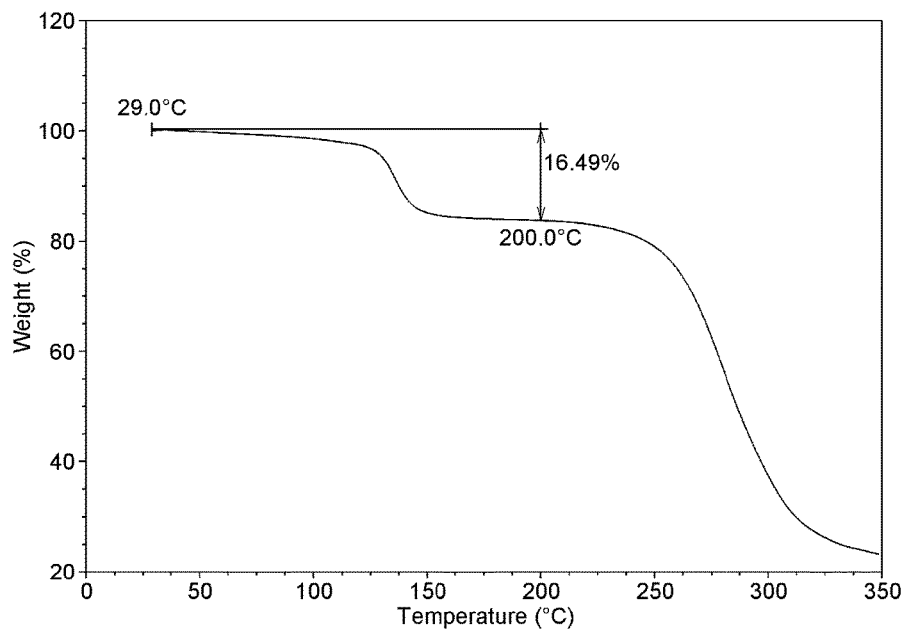
FIG. 7 shows a TGA thermogram of crystalline Form II
Figure 8:
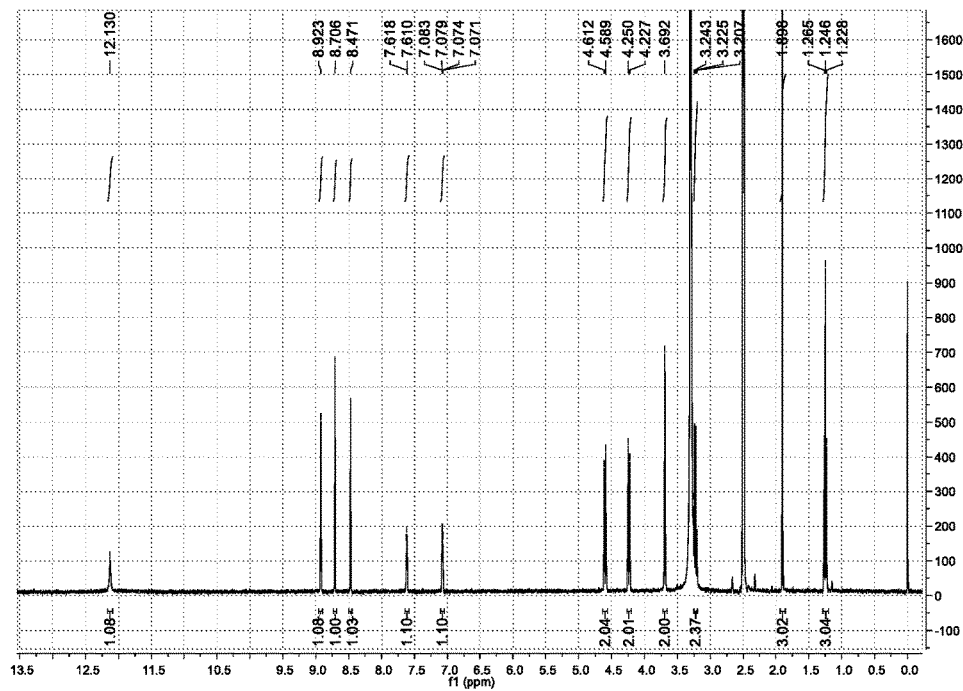
FIG. 8 shows a $^1$H NMR spectrum of crystalline Form II

The XRPD datas of the solid prepared in this example are listed in Table 3. The XRPD pattern is displayed in FIG. 5. The DSC thermogram is displayed in FIG. 6, the TGA thermogram is displayed in FIG. 7, the $^1$H NMR spectrum is displayed in FIG. 8, the $^1$H NMR datas are in the following:

$^1$H NMR (400 MHz, DMSO-d6) δ 12.13 (s, 1H), 8.92 (s, 1H), 8.71 (s, 1H), 8.47 (s, 1H), 7.62 (dd, J1=2.4 Hz, J2=3.2 Hz, 1H), 7.08 (dd, J1=1.2 Hz, J2=3.2 Hz, 1H), 4.60 (d, J=9.2 Hz, 2H), 4.24 (d, J=9.2 Hz, 2H), 3.69 (s, 2H), 3.23 (q, J=7.2 Hz, 2H), 1.90 (s, 3H), 1.25 (t, J=7.2 Hz, 3H)○

TABLE 3

| 2theta | d spacing | Relative intensity % |
|---|---|---|
| 7.26 | 12.18 | 80.22 |
| 9.31 | 9.50 | 16.60 |
| 10.87 | 8.14 | 94.25 |
| 11.21 | 7.89 | 29.44 |
| 12.14 | 7.29 | 59.63 |
| 14.60 | 6.07 | 68.00 |
| 15.10 | 5.87 | 4.89 |
| 16.96 | 5.23 | 4.01 |
| 17.52 | 5.06 | 18.17 |
| 18.00 | 4.93 | 100.00 |
| 19.33 | 4.59 | 5.61 |
| 19.64 | 4.52 | 18.18 |
| 19.96 | 4.45 | 4.49 |
| 20.73 | 4.29 | 0.89 |
| 21.27 | 4.18 | 3.69 |
| 22.03 | 4.03 | 19.86 |
| 22.42 | 3.96 | 13.33 |
| 22.59 | 3.94 | 24.49 |
| 23.60 | 3.77 | 5.99 |
| 24.18 | 3.68 | 1.69 |
| 25.67 | 3.47 | 6.76 |
| 26.70 | 3.34 | 3.41 |
| 27.30 | 3.27 | 3.07 |
| 27.53 | 3.24 | 5.43 |
| 28.28 | 3.16 | 2.93 |
| 28.84 | 3.10 | 5.32 |
| 29.51 | 3.03 | 17.10 |
| 29.92 | 2.99 | 4.03 |
| 30.55 | 2.93 | 1.16 |
| 31.07 | 2.88 | 1.20 |
| 31.78 | 2.82 | 4.30 |
| 34.22 | 2.62 | 5.60 |
| 35.54 | 2.53 | 1.72 |
| 37.42 | 2.40 | 1.93 |
| 38.49 | 2.34 | 1.02 |

Example 4

Process of Preparing Crystalline Form II of the Compound of Formula (I):

5.22 mg of compound of Formula (I) was dissolved into 0.1 mL of glacial acetic acid, and evaporated at room temperature, the obtained solid was detected as crystalline Form II.

The XRPD datas of the solid prepared in this example are listed in Table 4.

TABLE 4

| 2theta | d spacing | Relative intensity % |
|---|---|---|
| 7.27 | 12.16 | 64.39 |
| 9.31 | 9.50 | 63.85 |
| 10.87 | 8.14 | 99.37 |
| 11.21 | 7.89 | 26.31 |
| 12.14 | 7.29 | 49.51 |
| 14.61 | 6.06 | 57.03 |
| 15.08 | 5.88 | 4.74 |
| 17.51 | 5.07 | 22.95 |
| 18.00 | 4.93 | 100.00 |

TABLE 4-continued

| 2theta | d spacing | Relative intensity % |
|---|---|---|
| 19.63 | 4.52 | 15.32 |
| 19.96 | 4.45 | 11.72 |
| 22.01 | 4.04 | 18.45 |
| 22.29 | 3.99 | 11.02 |
| 22.57 | 3.94 | 17.52 |
| 23.60 | 3.77 | 6.34 |
| 25.64 | 3.47 | 6.00 |
| 26.70 | 3.34 | 5.23 |
| 27.51 | 3.24 | 5.33 |
| 28.29 | 3.15 | 7.97 |
| 28.83 | 3.10 | 6.43 |
| 29.52 | 3.03 | 17.04 |
| 31.79 | 2.82 | 4.23 |
| 34.22 | 2.62 | 4.17 |
| 35.53 | 2.53 | 2.34 |

Example 5

Figure 4:
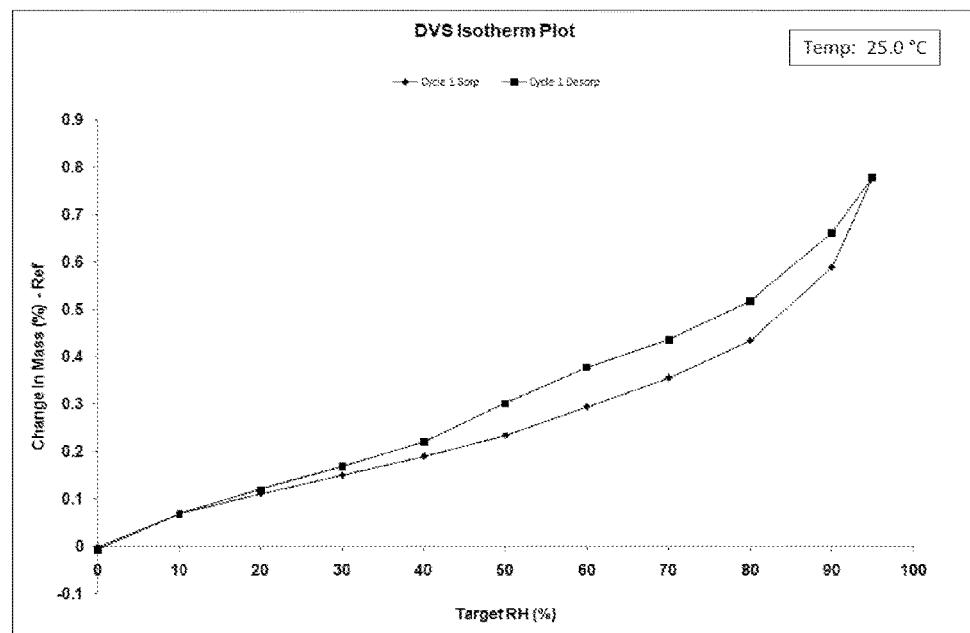
FIG. 4 shows a DVS plot of crystalline Form I

Hygroscopicity Assessment of Form I of the Compound Formula (I):

Hygroscopicity of 10 mg Form I of the present disclosure was tested using dynamic vapor sorption (DVS). The result is listed in Table. 5. The DVS isotherm plot is shown in FIG. 4.

TABLE 5

| Solid Form | weight gain under 80% Relative Humidity |
|---|---|
| Form I of the compound Formula (I) | 0.44% |

About hygroscopicity characterization description and definition of hygroscopicity (Chinese Pharmacopoeia 2010 edition appendix XIXJ Drug hygroscopic test guidelines, test at 25° C.+/−1° C., 80% Relative Humidity)

deliquescent: sufficient water is absorbed to form a liquid;

very hygroscopic: increase in mass is equal to or greater than 15 percent;

hygroscopic: increase in mass is less than 15 percent and equal to or greater than 2 percent;

slightly hygroscopic: increase in mass is less than 2 percent and equal to or greater than 0.2 percent.

no or almost no hygroscopic: increase in mass is less than 0.2%.

The result indicates that the weight gain of Form I of the compound Formula (I) of the present disclosure is 0.44% at 80% RH, according to the definition standard of hygroscopicity, Form I belongs to the slightly hygroscopic.

Example 6

Figure 9:
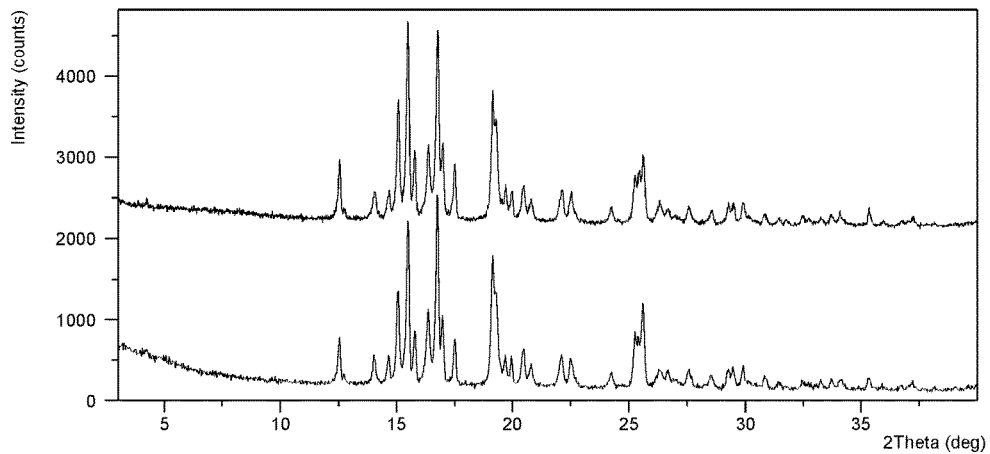
FIG. 9 shows an XRPD overlay pattern of crystalline Form I before and after storing at 5° C. for 90 days (the pattern above is before storing and the below one is after storing)
Figure 10:
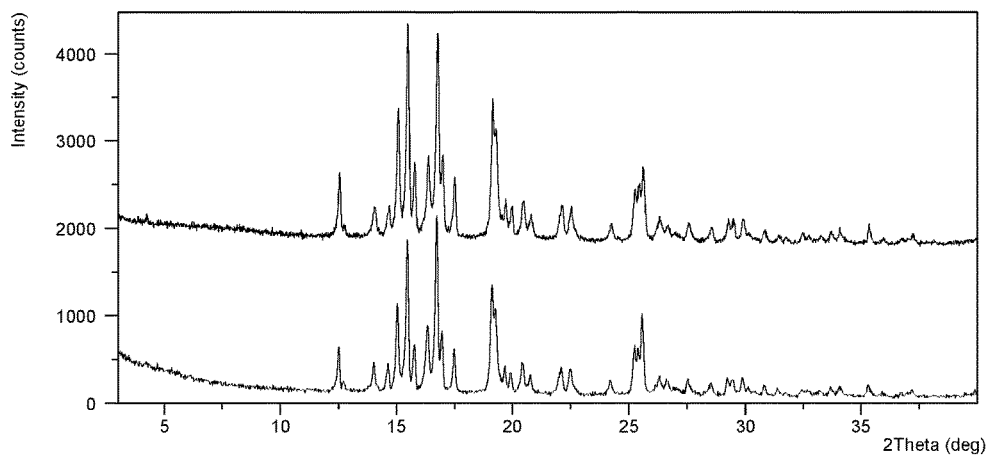
FIG. 10 shows an XRPD overlay pattern of crystalline Form I before and after storing at 25° C./60% RH for 90 days (the pattern above is before storing and the below one is after storing)
Figure 11:
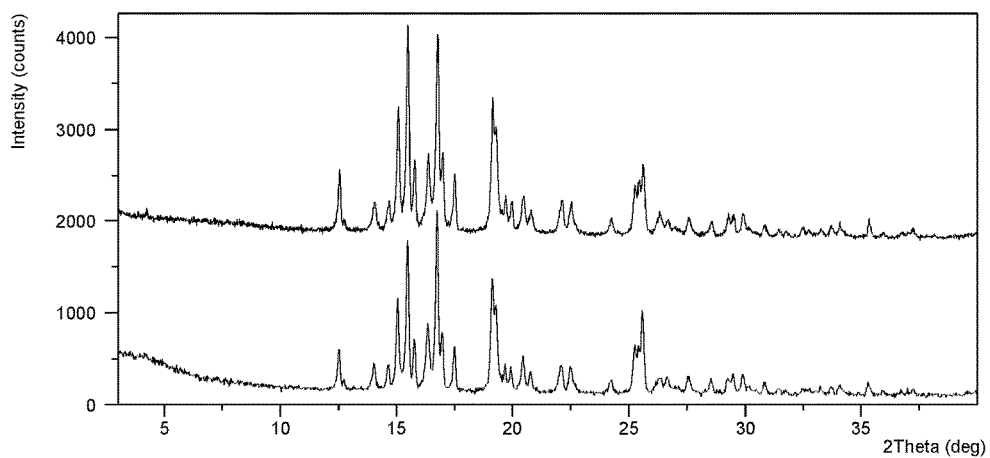
FIG. 11 shows an XRPD overlay pattern of crystalline Form I before and after storing at 40° C./75% RH for 90 days (the pattern above is before storing and the below one is after storing)

Stability Assessment of Form I of the Compound Formula (I):

The crystalline Form I of the present disclosure was stored under 5° C., 25° C./60% RH and 40° C./75% relative humidity for 90 days. XRPD patterns were collected after storage. The experiment result is shown in Table 6. The XRPD patterns of Form I before and after storing under the three stress conditions for 90 days are displayed in FIG. 9, FIG. 10 and FIG. 11 (the patterns above in FIG. 9, FIG. 10 and FIG. 11 were the XRPD patterns of Form I before storing).

TABLE 6

| Initial Form | conditions | Storage time | Form Change |
|---|---|---|---|
| Form I | 5° C. | 90 days | Form I remain unchanged (FIG. 9 below) |
|  | 25° C./60% RH | 90 days | Form I remain unchanged (FIG. 10 below) |
|  | 40° C./75% RH | 90 days | Form I remain unchanged (FIG. 11 below) |

The result indicates that crystalline Form I of the compound of Formula (I) remains unchanged after stored at 5° C., 25° C./60% RH and 40° C./75% RH for 90 days. The crystalline Form I of the compound of Formula (I) has good stability.

Example 7

Figure 12:
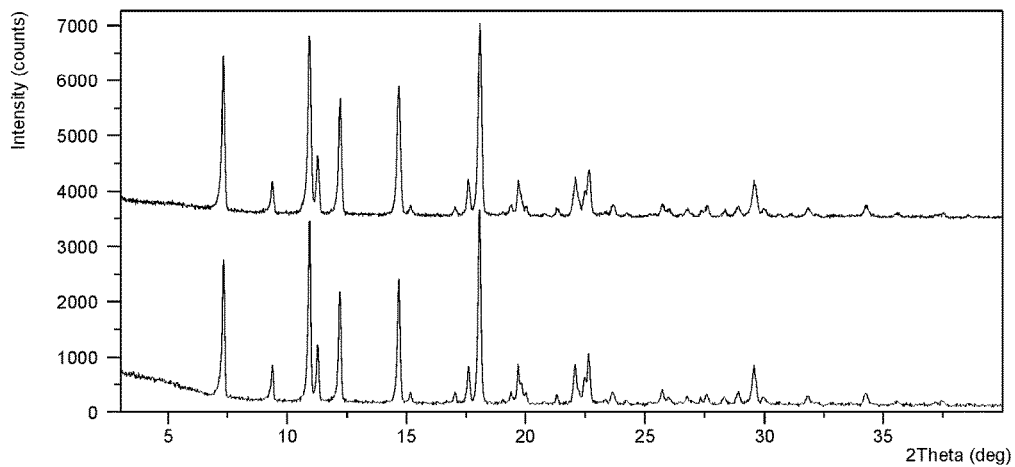
FIG. 12 shows an XRPD overlay pattern of crystalline Form II before and after storing at 5° C. for 90 days (the pattern above is before storing and the below one is after storing)
Figure 13:
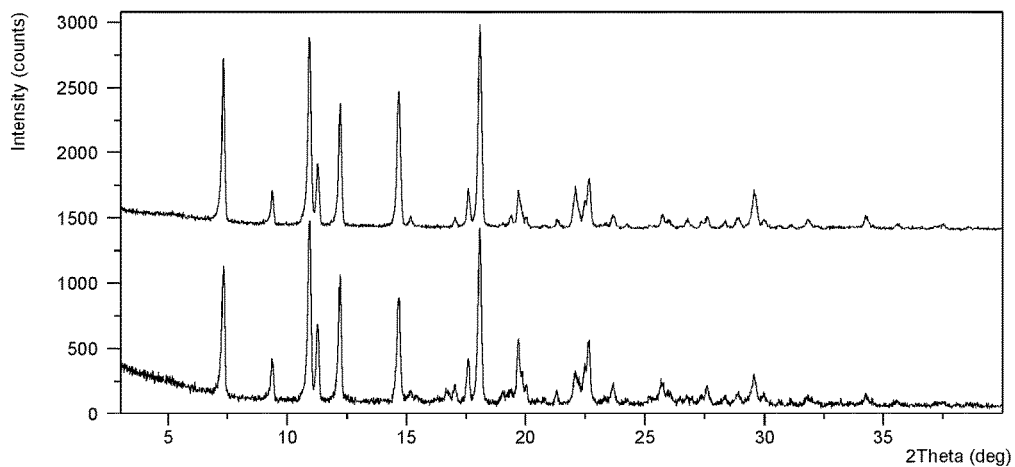
FIG. 13 shows an XRPD overlay pattern of crystalline Form II before and after storing at 25° C./60% RH for 30 days (the pattern above is before storing and the below one is after storing)

Stability Assessment of Form II of the Compound Formula (I):

The crystalline Form II of the present disclosure was stored under 5° C. and 25° C./60% RH. XRPD patterns were collected after storage. The experiment result is shown in Table 7. The XRPD patterns of Form II before and after storing under the two stress conditions are displayed in FIG. 12 and FIG. 13 (the patterns above in FIG. 12 and FIG. 13 were the XRPD patterns of Form II before storing).

TABLE 7

| Initial Form | conditions | Storage time | Form Change |
|---|---|---|---|
| Form II | 5° C. | 90 days | Form II remain unchanged (FIG. 12 below) |
|  | 25° C./60% RH | 30 days | Form II remain unchanged (FIG. 13 below) |

The result indicates that crystalline Form II of the compound of Formula (I) remains unchanged after stored at 5° C. for 90 days, 25° C./60% RH for 30 days. The crystalline Form II of the compound of Formula (I) has good stability.

Example 8

Process of Preparing Phosphate Crystalline Form A of the Compound of Formula (I):

502.6 mg of compound of Formula (I) was added into a mixed solvent of 12.5 mL of acetonitrile and 4.0 mL of ethanol to obtain a suspension, 90 μL of concentrated phosphoric acid (14.6 mol/L) dissolved in 1 mL of ethanol was dropwise added into the suspension, it was stirred for 24 hours at 70° C. in drying oven, then centrifuged to obtain a solid, placed the solid at a constant temperature of 25° C. overnight for drying, the obtained solid was detected as crystalline Form A.

Figure 14:
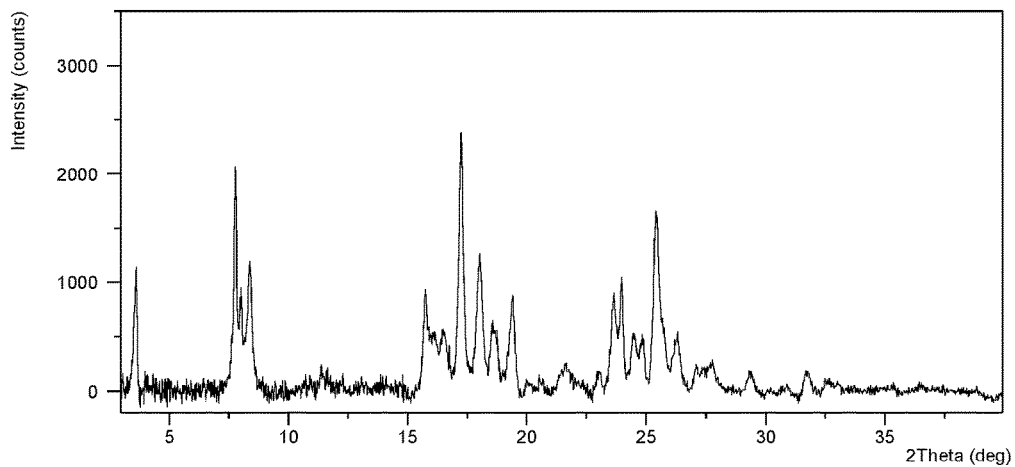
FIG. 14 shows an XRPD pattern of phosphate crystalline Form A
Figure 15:
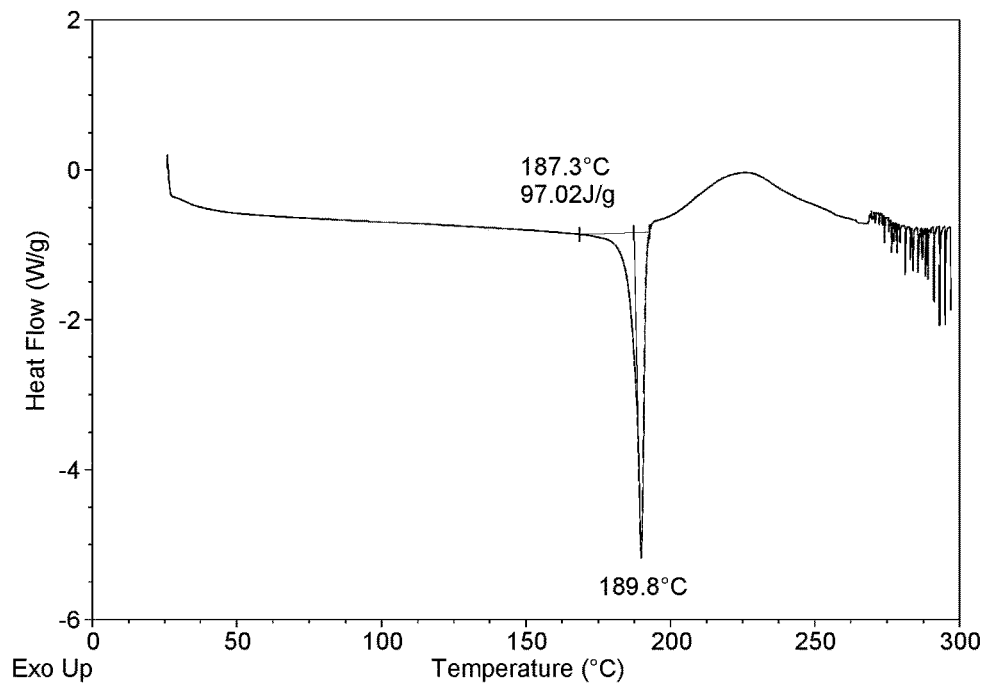
FIG. 15 shows a DSC thermogram of phosphate crystalline Form A
Figure 16:
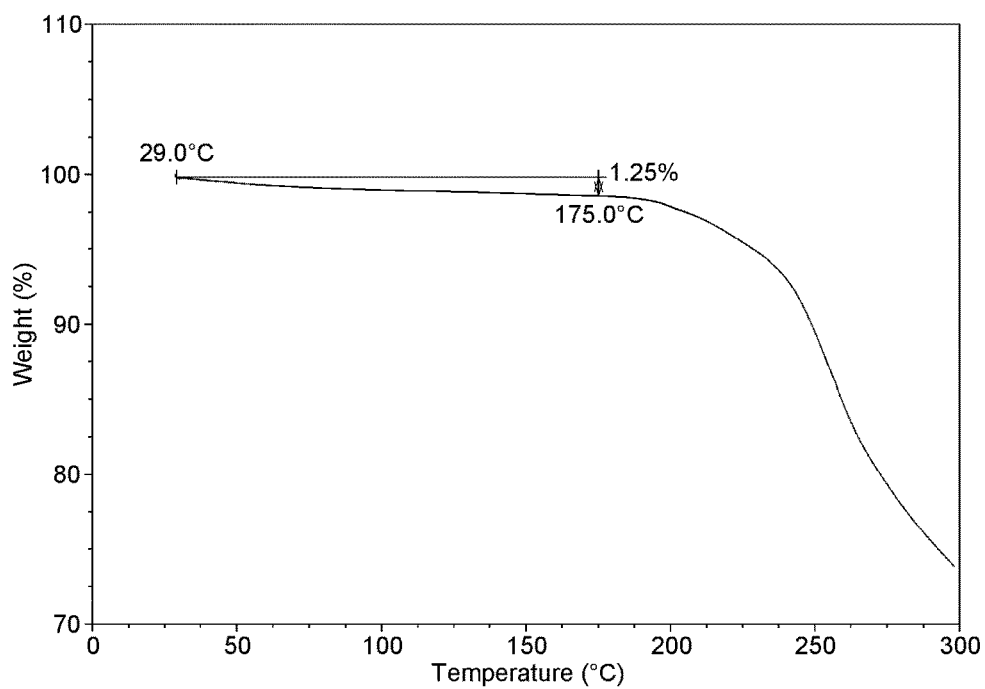
FIG. 16 shows a TGA thermogram of phosphate crystalline Form A

The XRPD datas of the solid prepared in this example are listed in Table 8. The XRPD pattern is displayed in FIG. 14. The DSC thermogram is displayed in FIG. 15, the TGA thermogram is displayed in FIG. 16.

TABLE 8

| 2theta | d spacing | Relative intensity % |
|---|---|---|
| 3.59 | 24.63 | 47.91 |
| 4.02 | 22.01 | 1.79 |
| 7.78 | 11.36 | 86.50 |

TABLE 8-continued

| 2theta | d spacing | Relative intensity % |
|---|---|---|
| 8.00 | 11.05 | 37.44 |
| 8.38 | 10.55 | 49.77 |
| 10.65 | 8.31 | 2.31 |
| 11.51 | 7.69 | 4.68 |
| 12.20 | 7.25 | 3.22 |
| 13.07 | 6.78 | 3.32 |
| 14.14 | 6.26 | 1.98 |
| 15.72 | 5.64 | 38.58 |
| 16.48 | 5.38 | 22.57 |
| 17.22 | 5.15 | 100.00 |
| 17.99 | 4.93 | 50.58 |
| 18.55 | 4.78 | 25.56 |
| 19.40 | 4.58 | 36.35 |
| 20.00 | 4.44 | 3.83 |
| 20.59 | 4.31 | 2.57 |
| 21.62 | 4.11 | 9.41 |
| 23.03 | 3.86 | 7.56 |
| 23.62 | 3.77 | 35.97 |
| 23.96 | 3.71 | 43.13 |
| 24.47 | 3.64 | 21.25 |
| 24.83 | 3.59 | 19.98 |
| 25.40 | 3.51 | 68.63 |
| 26.27 | 3.39 | 20.98 |
| 27.09 | 3.29 | 9.50 |
| 27.79 | 3.21 | 8.59 |
| 29.34 | 3.04 | 6.23 |
| 30.90 | 2.89 | 2.07 |
| 31.73 | 2.82 | 6.85 |
| 32.75 | 2.73 | 2.71 |
| 35.15 | 2.55 | 0.90 |
| 36.51 | 2.46 | 2.17 |

Example 9

Process of Preparing Phosphate Crystalline Form A of the Compound of Formula (I):

100.4 mg of compound of Formula (I) was added into a mixed solvent of 2.5 mL of acetonitrile and 0.79 mL of ethanol to obtain a suspension, 17.7 μL of concentrated phosphoric acid (14.6 mol/L) dissolved in 390 μL of ethanol was dropwise added into the suspension liquid, it was stirred for 24 hours at 70° C. in drying oven, then centrifuged to obtain a lower layer of solid, placed the solid at a constant temperature of 25° C. overnight for drying, the obtained solid was detected as phosphate crystalline Form A.

The XRPD datas of the solid prepared in this example are listed in Table 9.

TABLE 9

| 2theta | d spacing | Relative intensity % |
|---|---|---|
| 3.56 | 24.79 | 77.29 |
| 7.78 | 11.36 | 73.30 |
| 8.37 | 10.57 | 61.12 |
| 11.52 | 7.68 | 4.20 |
| 14.77 | 6.00 | 5.34 |
| 15.72 | 5.64 | 23.84 |
| 17.20 | 5.15 | 100.00 |
| 18.00 | 4.93 | 48.24 |
| 18.55 | 4.78 | 45.75 |
| 19.42 | 4.57 | 49.05 |
| 20.56 | 4.32 | 6.53 |
| 21.63 | 4.11 | 8.99 |
| 23.96 | 3.71 | 37.14 |
| 25.38 | 3.51 | 52.10 |
| 26.24 | 3.40 | 21.72 |
| 27.67 | 3.22 | 9.74 |
| 29.36 | 3.04 | 5.10 |
| 31.74 | 2.82 | 4.01 |

TABLE 9-continued

| 2theta | d spacing | Relative intensity % |
|---|---|---|
| 35.18 | 2.55 | 2.21 |
| 36.89 | 2.44 | 1.16 |

Example 10

Process of Preparing Phosphate Crystalline Form B of the Compound of Formula (I):

503.4 mg of compound of Formula (I) was added into 15.0 mL methyl isobutyl ketone to obtain a suspension, adding 0.14 mL of concentrated phosphoric acid (14.6 mol/L), then it was stirred at room temperature for 24 hours, centrifuged to obtain a lower layer of solid, placed the solid at a constant temperature of 25° C. overnight for drying, the obtained solid was detected as phosphate crystalline Form B.

Figure 17:
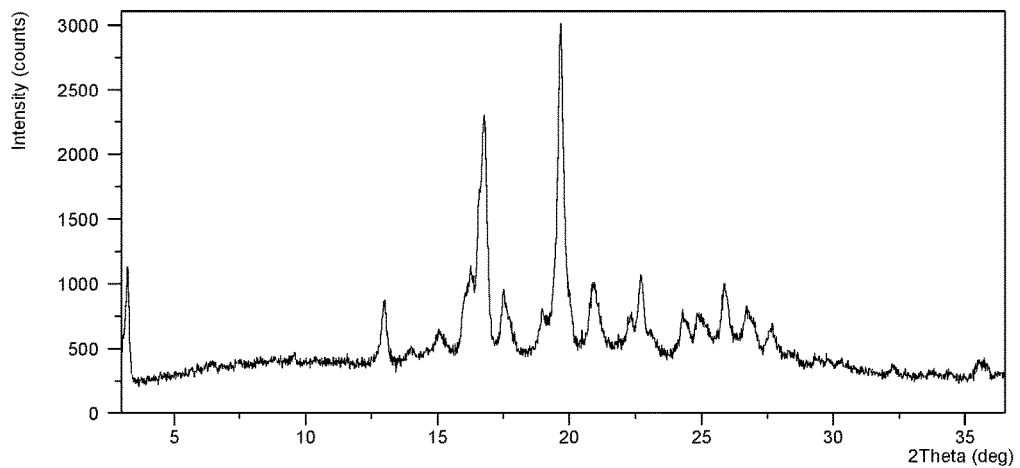
FIG. 17 shows an XRPD pattern of phosphate crystalline Form B
Figure 18:
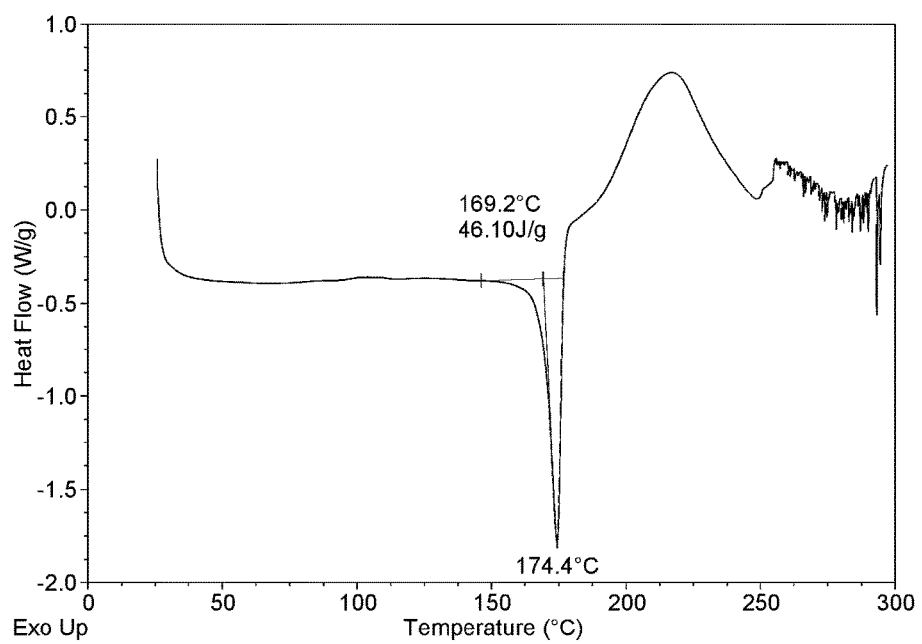
FIG. 18 shows a DSC thermogram of phosphate crystalline Form B
Figure 19:
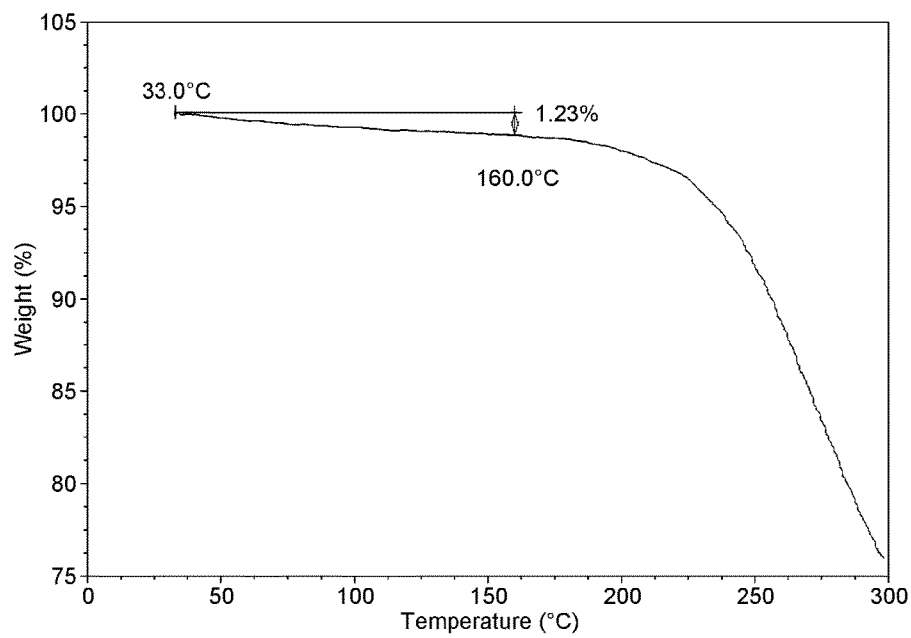
FIG. 19 shows a TGA thermogram of phosphate crystalline Form B

The XRPD datas of the solid prepared in this example are listed in Table 10. The XRPD pattern is displayed in FIG. 17. The DSC thermogram is displayed in FIG. 18, the TGA thermogram is displayed in FIG. 19.

TABLE 10

| 2theta | d spacing | Relative intensity % |
|---|---|---|
| 3.19 | 27.66 | 32.85 |
| 12.92 | 6.85 | 16.82 |
| 13.93 | 6.36 | 4.49 |
| 15.02 | 5.90 | 9.60 |
| 15.94 | 5.56 | 18.35 |
| 16.21 | 5.47 | 27.78 |
| 16.71 | 5.30 | 73.18 |
| 17.47 | 5.08 | 22.00 |
| 18.94 | 4.69 | 16.40 |
| 19.62 | 4.52 | 100.00 |
| 20.88 | 4.25 | 24.03 |
| 22.28 | 3.99 | 15.79 |
| 22.67 | 3.92 | 27.33 |
| 24.25 | 3.67 | 16.12 |
| 24.87 | 3.58 | 15.91 |
| 25.82 | 3.45 | 24.63 |
| 26.67 | 3.34 | 18.05 |
| 27.59 | 3.23 | 12.70 |
| 29.98 | 2.98 | 3.28 |
| 32.23 | 2.78 | 2.89 |
| 35.53 | 2.53 | 3.80 |

Example 11

Process of Preparing Phosphate Crystalline Form B of the Compound of Formula (I):

10.6 mg of compound of Formula (I) was added into 0.8 mL isopropyl acetate to obtain a suspension, added 17 mL phosphoric acid ethanol solution (2 mol/L), put the turbid liquid into a 50° C. constant temperature incubator and stirred for 24 hours, centrifuged to obtain a lower layer of solid, placed the solid at a constant temperature of 25° C. for drying overnight, the obtained solid was detected as phosphate crystalline Form B.

The XRPD datas of the solid prepared in this example are listed in Table 11.

TABLE 11

| 2theta | d spacing | Relative intensity % |
|---|---|---|
| 3.24 | 27.28 | 100.00 |
| 8.32 | 10.63 | 5.04 |

TABLE 11-continued

| 2theta | d spacing | Relative intensity % |
|---|---|---|
| 8.82 | 10.02 | 6.26 |
| 10.39 | 8.52 | 1.92 |
| 12.93 | 6.85 | 10.87 |
| 15.04 | 5.89 | 15.51 |
| 16.00 | 5.54 | 18.40 |
| 16.23 | 5.46 | 23.52 |
| 16.76 | 5.29 | 85.35 |
| 17.60 | 5.04 | 9.37 |
| 19.10 | 4.65 | 9.10 |
| 19.62 | 4.52 | 30.64 |
| 19.90 | 4.46 | 10.74 |
| 20.95 | 4.24 | 15.77 |
| 22.23 | 4.00 | 6.65 |
| 22.68 | 3.92 | 5.50 |
| 25.13 | 3.54 | 18.70 |
| 25.87 | 3.44 | 26.35 |
| 26.36 | 3.38 | 18.62 |
| 26.69 | 3.34 | 24.91 |
| 27.54 | 3.24 | 9.69 |
| 30.12 | 2.97 | 1.69 |
| 35.73 | 2.51 | 1.14 |

Example 12

Process of Preparing Phosphate Crystalline Form C of the Compound of Formula (I):

10.2 mg of phosphate crystalline Form B of compound of Formula (I) was added into a mixed solvent of 0.97 mL of acetonitrile and 0.03 mL of water to obtain a suspension, then it was stirred at 25° C. for 12 hours, centrifuged to obtain a lower layer of solid, placed the solid at a constant temperature of 25° C. for drying overnight, the obtained solid was detected as phosphate crystalline Form C.

Figure 20:
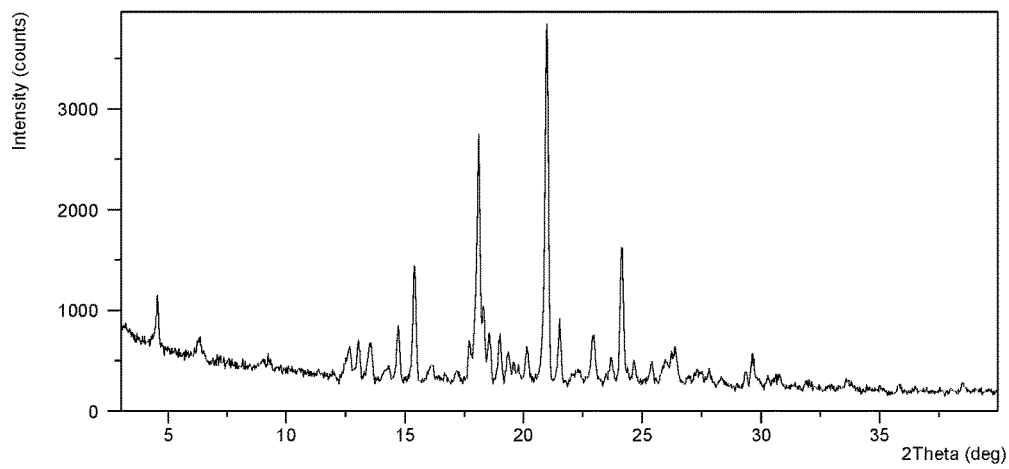
FIG. 20 shows an XRPD pattern of phosphate crystalline Form C
Figure 21:
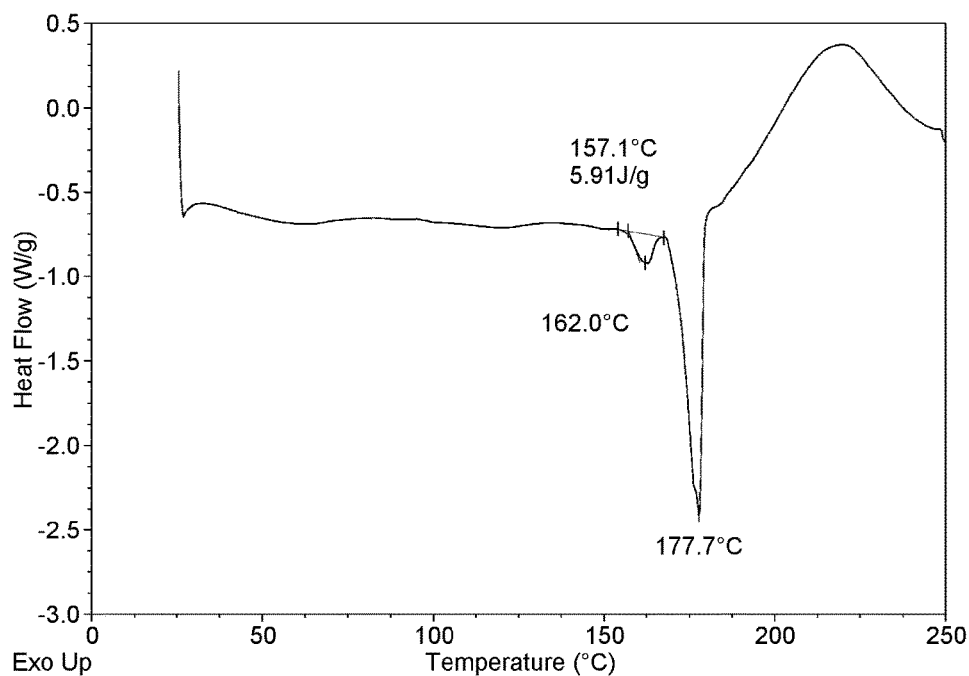
FIG. 21 shows a DSC thermogram of phosphate crystalline Form C
Figure 22:
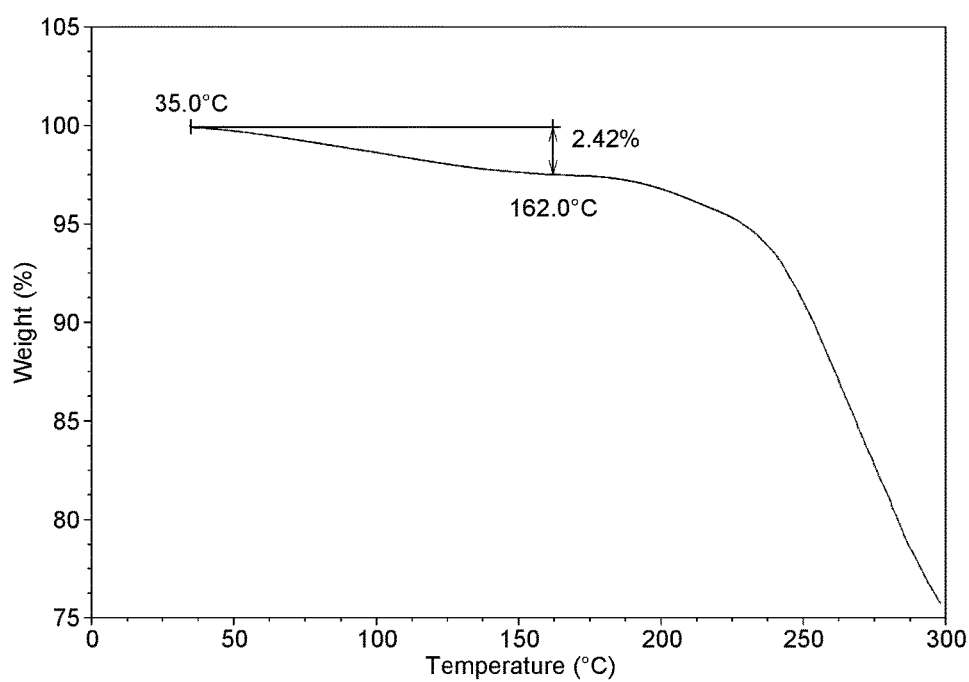
FIG. 22 shows a TGA thermogram of phosphate crystalline Form C

The XRPD datas of the solid prepared in this example are listed in Table 12. The XRPD pattern is displayed in FIG. 20. The DSC thermogram is displayed in FIG. 21, the TGA thermogram is displayed in FIG. 22.

TABLE 12

| 2theta | d spacing | Relative intensity % |
|---|---|---|
| 4.47 | 19.77 | 13.51 |
| 6.25 | 14.15 | 5.34 |
| 9.04 | 9.78 | 1.84 |
| 12.54 | 7.06 | 7.86 |
| 12.94 | 6.84 | 9.99 |
| 13.43 | 6.59 | 8.85 |
| 14.62 | 6.06 | 14.06 |
| 15.29 | 5.79 | 31.90 |
| 16.01 | 5.54 | 3.92 |
| 18.01 | 4.93 | 67.14 |
| 18.23 | 4.87 | 20.45 |
| 18.49 | 4.80 | 11.46 |
| 18.91 | 4.69 | 11.53 |
| 19.25 | 4.61 | 7.95 |
| 20.07 | 4.42 | 9.37 |
| 20.90 | 4.25 | 100.00 |
| 21.44 | 4.14 | 17.65 |
| 22.12 | 4.02 | 3.14 |
| 22.83 | 3.89 | 13.11 |
| 23.62 | 3.77 | 7.02 |
| 24.05 | 3.70 | 38.78 |
| 24.57 | 3.62 | 6.29 |
| 25.29 | 3.52 | 6.28 |
| 26.31 | 3.39 | 9.73 |
| 29.56 | 3.02 | 9.41 |
| 30.65 | 2.92 | 3.22 |
| 33.62 | 2.67 | 2.35 |

Example 13

Process of Preparing Phosphate Crystalline Form C of the Compound of Formula (I):

9.6 mg of phosphate crystalline Form B of compound of Formula (I) was added into a mixed solvent of 0.95 mL of acetonitrile and 0.05 mL of water to obtain a suspension, then it was stirred at 25° C. for 12 hours, centrifuged to obtain a lower layer of solid, placed the solid at a constant temperature of 25° C. for drying overnight, the obtained solid was detected as phosphate crystalline Form C.

The XRPD data of the solid prepared in this example are listed in Table 13.

TABLE 13

| 2theta | d spacing | Relative intensity % |
|---|---|---|
| 4.46 | 19.82 | 5.24 |
| 6.22 | 14.20 | 2.24 |
| 7.43 | 11.90 | 0.94 |
| 9.07 | 9.75 | 0.69 |
| 12.59 | 7.03 | 3.64 |
| 12.97 | 6.82 | 1.55 |
| 13.45 | 6.58 | 7.05 |
| 14.63 | 6.05 | 10.26 |
| 15.33 | 5.78 | 4.93 |
| 15.91 | 5.57 | 0.86 |
| 16.58 | 5.35 | 1.99 |
| 17.64 | 5.03 | 7.13 |
| 18.01 | 4.93 | 31.58 |
| 18.49 | 4.80 | 3.21 |
| 18.94 | 4.69 | 4.87 |
| 19.29 | 4.60 | 2.19 |
| 20.09 | 4.42 | 3.55 |
| 20.90 | 4.25 | 100.00 |
| 21.45 | 4.14 | 6.89 |
| 22.84 | 3.89 | 5.46 |
| 24.13 | 3.69 | 5.67 |
| 24.64 | 3.61 | 1.51 |
| 25.33 | 3.52 | 4.97 |
| 25.91 | 3.44 | 3.13 |
| 26.24 | 3.40 | 2.17 |
| 27.20 | 3.28 | 2.52 |
| 29.27 | 3.05 | 3.37 |
| 29.58 | 3.02 | 3.35 |
| 30.60 | 2.92 | 0.85 |
| 31.89 | 2.81 | 1.26 |
| 33.63 | 2.67 | 1.73 |
| 35.00 | 2.56 | 0.75 |

Example 14

Process of Preparing Phosphate Crystalline Form C of the Compound of Formula (I):

8.0 mg of phosphate crystalline Form B of compound of Formula (I) was added into a mixed solvent of 0.97 mL of acetonitrile and 0.03 mL of water to obtain a suspension, then it was stirred at 40° C. for 12 hours, centrifuged to obtain a lower layer of solid, placed the solid at a constant temperature of 25° C. overnight for drying, the obtained solid was detected as phosphate crystalline Form C.

The XRPD datas of the solid prepared in this example are listed in Table 14.

TABLE 14

| 2theta | d spacing | Relative intensity % |
|---|---|---|
| 3.29 | 26.83 | 37.61 |
| 4.45 | 19.85 | 33.84 |
| 6.23 | 14.18 | 13.30 |
| 12.54 | 7.06 | 6.59 |

TABLE 14-continued

| 2theta | d spacing | Relative intensity % |
|---|---|---|
| 12.96 | 6.83 | 9.58 |
| 13.47 | 6.57 | 12.44 |
| 14.18 | 6.24 | 4.38 |
| 14.62 | 6.06 | 14.36 |
| 15.32 | 5.78 | 18.20 |
| 17.64 | 5.03 | 8.32 |
| 18.02 | 4.92 | 50.92 |
| 18.27 | 4.86 | 10.99 |
| 18.48 | 4.80 | 8.86 |
| 18.94 | 4.69 | 9.36 |
| 19.26 | 4.61 | 5.60 |
| 20.05 | 4.43 | 5.38 |
| 20.90 | 4.25 | 100.00 |
| 21.45 | 4.14 | 10.37 |
| 22.83 | 3.89 | 5.93 |
| 24.09 | 3.69 | 15.36 |
| 24.57 | 3.62 | 4.42 |
| 25.34 | 3.52 | 4.34 |
| 25.89 | 3.44 | 5.23 |
| 26.24 | 3.40 | 5.98 |
| 29.40 | 3.04 | 1.24 |

Example 15

Figure 23:
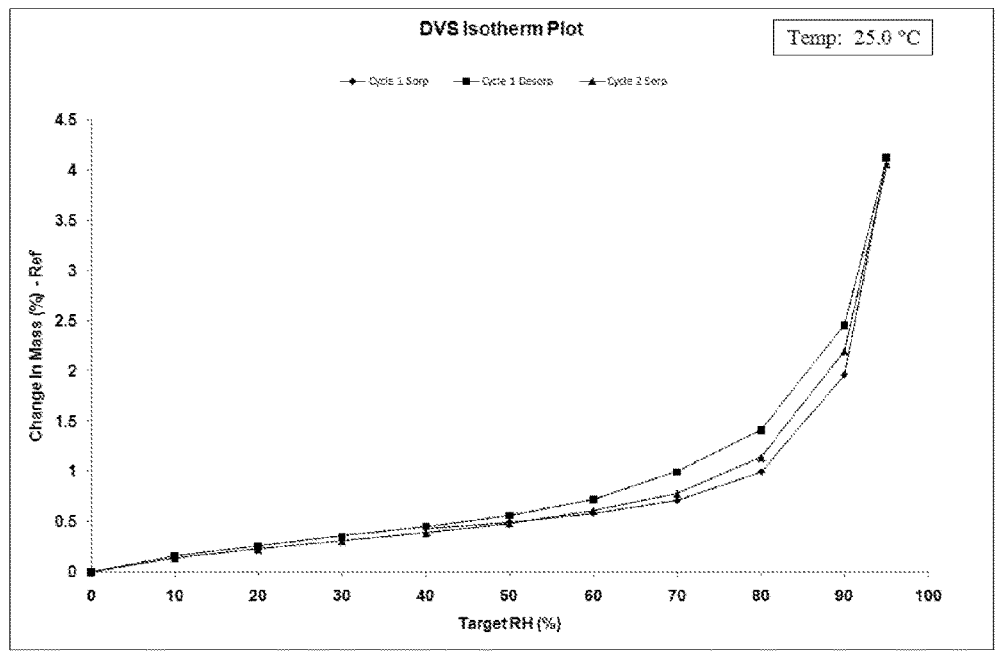
FIG. 23 shows a DVS plot of phosphate crystalline Form A
Figure 24:
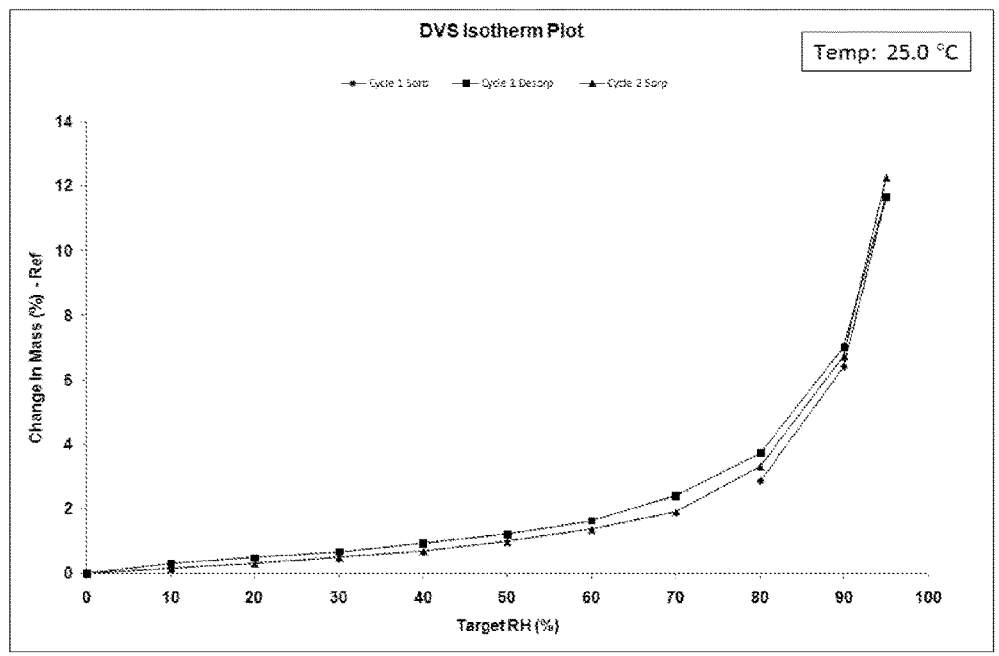
FIG. 24 shows a DVS plot of phosphate crystalline Form C

Hygroscopicity Assessment of Phosphate Crystalline Form A and Phosphate Crystalline Form C of the Compound Formula (I):

Hygroscopicity of 10 mg of phosphate crystalline Form A and phosphate crystalline Form C of the present disclosure were tested using dynamic vapor sorption (DVS). The results are listed in Table 15. The DVS plot of phosphate crystalline Form A is shown in FIG. 23, The DVS plot of phosphate crystalline Form C is shown in FIG. 24.

TABLE 15

| Solid Form | weight gain under 80% Relative Humidity |
|---|---|
| phosphate Form A of the compound Formula (I) | 0.99% |
| phosphate Form C of the compound Formula (I) | 2.85% |

About hygroscopicity characterization description and definition of hygroscopicity (Chinese Pharmacopoeia 2010 edition appendix XIXJ Drug hygroscopic test guidelines, test at 25° C.+/−1° C., 80% Relative Humidity)

deliquescent: sufficient water is absorbed to form a liquid;
very hygroscopic: increase in mass is equal to or greater than 15 percent;
hygroscopic: increase in mass is less than 15 percent and equal to or greater than 2 percent;
slightly hygroscopic: increase in mass is less than 2 percent and equal to or greater than 0.2 percent.
no or almost no hygroscopic: increase in mass is less than 0.2%.

The result indicates that the weight gain of phosphate Form A and phosphate Form C of the compound Formula (I) are increased by 0.99% and 2.85% respectively at 80% Relative Humidity.

Example 16

Stability Assessment of Phosphate Form A of the Compound Formula (I):

Phosphate Form A of the present disclosure was stored under 5° C., 25° C./60% RH and 40° C./75% RH for 90 days. XRPD patterns were collected after storage. The experiment result is shown in Table 16.

TABLE 16

| Initial Form | conditions | Storage time | Form Change |
|---|---|---|---|
| Phosphate Crystalline Form A | 5° C. | 90 days | Form A remain unchanged |
| | 25° C./60% RH | 90 days | Form A remain unchanged |
| | 40° C./75% RH | 90 days | Form A remain unchanged |

The result indicates that phosphate Form A of the compound of Formula (I) remains unchanged after stored at 5° C., 25° C./60% RH and 40° C./75% RH for 90 days. The phosphate Form A of the compound of Formula (I) has good stability.

Example 17

Stability Assessment of Phosphate Form C of the Compound Formula (I):

Two of 10 mg of phosphate Form C were respectively opened stored at 25° C./60% RH and 40° C./75% RH for 30 days. XRPD and purity of the sample were collected after storage. The experiment result is shown in Table 17. The XRPD patterns of phosphate Form C before and after storing under the two stress conditions for 30 days are displayed in FIG. 25 and FIG. 26 (the patterns above in FIG. 25 and FIG. 26 were the XRPD patterns of phosphate Form C before storing, below one in FIG. 25 was after storing under 25° C./60% RH for 30 days, below one in FIG. 25 was after storing under 40° C./75% RH for 30 days).

TABLE 17

Figure 25:
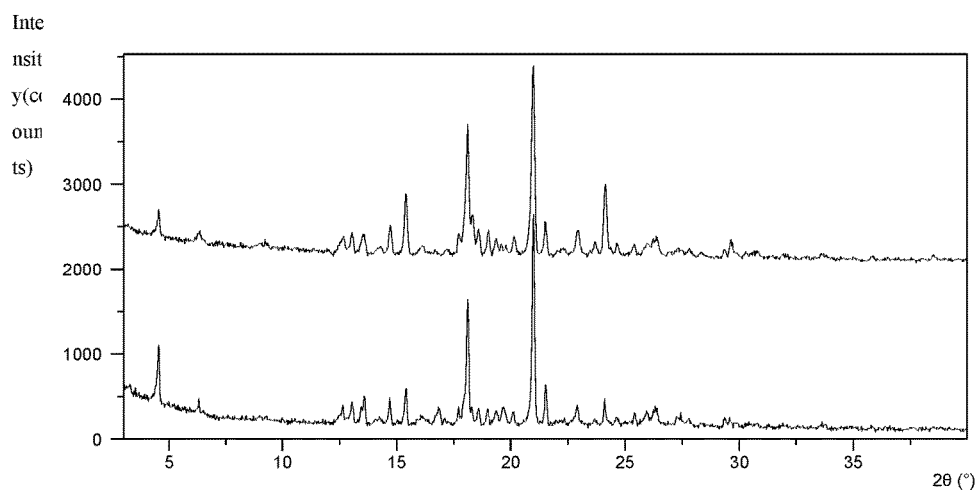
FIG. 25 shows an XRPD overlay pattern of phosphate crystalline Form C before and after storing at 25° C./60% RH for 30 days (the pattern above is before storing and the below one is after storing)
Figure 26:
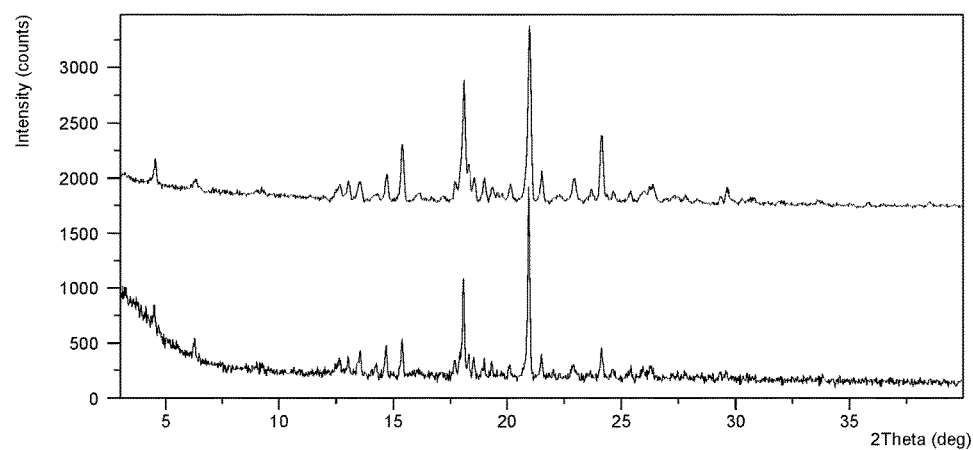
FIG. 26 shows an XRPD overlay pattern of phosphate crystalline Form C before and after storing at 40° C./75% RH for 30 days (the pattern above is before storing and the below one is after storing)

| Initial Form | Conditions | Storage time | Form Change | Comparison graph |
|---|---|---|---|---|
| Phosphate Form C | 25° C./60% RH | 30 days | Form C remain unchanged | FIG. 25 |
| | 40° C./75% RH | 30 days | Form C remain unchanged | FIG. 26 |

What is claimed is:

1. A crystalline Form II of {1-(ethylsulfonyl))-3-[4-(7H-pyrrolo[2,3-d]pyrimidine-4-yl)-1H-pyrazol-1-yl]azetidine-3-yl}acetonitrile, wherein the X-ray powder diffraction pattern shows characteristic peaks at 2theta values of 18.00°±0.20°, 10.80°±0.20° and 7.26°±0.20°.

* * * * *